United States Patent
Chen et al.

(10) Patent No.: US 7,776,891 B2
(45) Date of Patent: *Aug. 17, 2010

(54) VLA-4 ANTAGONISTS

(75) Inventors: Weichao Chen, San Diego, CA (US); Alec D. Lebsack, San Diego, CA (US); Benito Munoz, San Diego, CA (US); Shankar Venkatraman, San Diego, CA (US); Bowei Wang, San Diego, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 50 days.

This patent is subject to a terminal disclaimer.

(21) Appl. No.: 11/659,608

(22) PCT Filed: Aug. 12, 2005

(86) PCT No.: PCT/US2005/028768

§ 371 (c)(1),
(2), (4) Date: Feb. 6, 2007

(87) PCT Pub. No.: WO02/074761

PCT Pub. Date: Sep. 26, 2002

(65) Prior Publication Data

US 2007/0219252 A1    Sep. 20, 2007

Related U.S. Application Data

(60) Provisional application No. 60/601,942, filed on Aug. 16, 2004.

(51) Int. Cl.
*A61K 31/44* (2006.01)
*C07D 401/02* (2006.01)

(52) U.S. Cl. .......... 514/343; 546/278.4; 514/19

(58) Field of Classification Search .......... None
See application file for complete search history.

(56) References Cited

U.S. PATENT DOCUMENTS

| | | |
|---|---|---|
| 6,229,011 B1 | 5/2001 | Chen et al. |
| 6,288,267 B1 | 9/2001 | Hull et al. |
| 6,291,511 B1 | 9/2001 | Durette et al. |
| 6,388,084 B1 | 5/2002 | Kaplan et al. |
| 6,559,174 B2 | 5/2003 | Lin et al. |
| 6,583,139 B1 | 6/2003 | Thorsett et al. |
| 6,806,365 B2 | 10/2004 | Chen et al. |
| 6,855,706 B2 | 2/2005 | Tanaka et al. |
| 6,855,708 B2 | 2/2005 | Lin et al. |
| 6,903,075 B1 | 6/2005 | Durette et al. |
| 6,943,180 B2 | 9/2005 | Doherty et al. |
| 7,008,949 B2 | 3/2006 | Konradi et al. |
| 2007/0179190 A1 | 8/2007 | Hagmann et al. |

FOREIGN PATENT DOCUMENTS

| | | | |
|---|---|---|---|
| WO | WO 02/074761 | * | 9/2002 |
| WO | WO 02/074761 A1 | | 9/2002 |

OTHER PUBLICATIONS

Patani et al.: Bioisosterism: A rational approach in drug design. Chem Rev, 96:3147-3176, 1996.*
Doherty, G. A. et al., "N-Isonicotinoyl-(L)-4-aminophenylalanine Derivatives as Tight Binding VLA-4 Antagonists", Bioorganic & Medicinal Chemistry Letters, vol. 13, pp. 1891-1895, 2003.
McComas, C. C. et al., "Synthesis and Evaluation of Methyl Ether Derivatives of the Vancomycin, Teicoplanin, and Ristocetin Aglycon Methyl Esters", Bioorganic & Medicinal Chemistry Letters, vol. 13, pp. 2933-2936, 2003.
Lin et al., "Very late antigen 4 (VLA4) antagonists as anti-flammatory agents," Current Opinion in Chemical Biology, vol. 2, p. 453-457, 1998.
Yang et al., "VLA-4 Antagonists: Potent Inhibitors of Lymphocyte Migration," Medicinal Research Reviews, vol. 23, No. 3, p. 369-392, 2003.
Lobb et al., "Small molecule antagonists of alpha-4 integrins: novel drugs for asthma," Expert Opinion on Investigational Drugs, vol. 8, p. 935-945, 1999.
Tilley, "VLA-4 antagonists," Expert Opinion on Ther. Patents, vol. 12, No. 7, p. 991-1008, 2002.

* cited by examiner

*Primary Examiner*—Brian-Yong S Kwon
*Assistant Examiner*—Bong-Sook Baek
(74) *Attorney, Agent, or Firm*—Mollie M. Yang; Valerie J. Camara

(57) ABSTRACT

Compounds of Formula (I) are antagonists of VLA-4, and as such are useful in the inhibition or prevention of cell adhesion and cell-adhesion mediated pathologies. These compounds may be formulated into pharmaceutical compositions and are suitable for use in the treatment of inflammatory bowel disease including ulcerative colitis and Crohn's disease, multiple sclerosis, asthma, and rheumatoid arthritis.

2 Claims, No Drawings

VLA-4 ANTAGONISTS

CROSS REFERENCE TO RELATED APPLICATIONS

This application is the National Stage of International Application No. PCT/US2005/028768, filed 12 Aug. 2005 which claims the benefit under 35 U.S.C. 119(e) of U.S. Provisional Application No. 60/601,942 filed 16 Aug. 2004.

BACKGROUND OF THE INVENTION

VLA-4 ("very late antigen-4"; CD49d/CD29; or $\alpha_4\beta_1$) is an integrin expressed on all leukocytes, except platelets and mature neutrophils, including dendritic cells and macrophage-like cells and is a key mediator of the cell-cell and cell-matrix interactions of these cell types. The ligands for VLA-4 include vascular cell adhesion molecule-1 (VCAM-1), the CS-1 domain of fibronectin (FN), and the matrix protein, osteopontin. Neutralizing anti-$\alpha_4$ antibodies or blocking peptides that inhibit the interaction between VLA-4 and its ligands have been shown to be efficacious both prophylactically and therapeutically in several animal models of disease including asthma, multiple sclerosis, inflammatory bowel disease, and rheumatoid arthritis.

The humanized monoclonal antibody against $\alpha_4$, natalizumab (Antegren®, Elan/Biogen), has demonstrated efficacy in the treatment of multiple sclerosis (D. H. Miller et al., *New England Journal of Medicine*, 348, 15 (2003)) and Crohn's disease (S. Ghosh et al. *New England Journal of Medicine*, 348, 23 (2003)). There are also several VLA-4 antagonists in early clinical trials for treatment of asthma, arthritis, multiple sclerosis, and Crohn's disease.

In the early clinical trials with natalizumab, lymphocytosis (a surrogate marker for blockade of VLA-4 function) and >80% receptor occupancy were observed. A small molecule VLA-4 antagonist was reported to demonstrate functional activity in the rat experimental autoimmune encephalomyelitis (EAE) assay, an animal model of multiple sclerosis following subcutaneous administration (D. R. Leone et al., *J. Pharmacol. Exper. Therap.*, 305, 1150 (2003). This compound was shown to induce lymphocytosis, and to have a slow dissociation rate (off-rate) resulting in significant and sustained receptor occupancy on VLA-4-bearing cells. There was a positive correlation between receptor occupancy, lymphocytosis, and efficacy in the EAE model described in this manuscript.

A series of isonicotinoyl-L-aminophenylalanine derivatives shown to possess slow dissociation (off-rate) from VLA-4 on Jurkat cells were reported in G. Doherty et al., *Bioorganic & Medicinal Chemistry Letters*, 13, 1891 (2003). However, the compound that was further characterized demonstrated very poor pharmacokinetic properties such as low oral bioavailability, moderate to high plasma clearance and a short half-life rendering it unsuitable for oral administration. Compounds of the present invention are potent antagonists of VLA-4 capable of achieving and maintaining receptor occupancy for a time sufficient to allow for oral administration.

SUMMARY OF THE INVENTION

Substituted N-[N-benzenesulfonyl-prolyl]-phenylalanine derivatives of the present invention are antagonists of the VLA-4 integrin and are useful in the treatment, prevention and suppression of diseases mediated by VLA-4-binding and cell adhesion and activation. Moreover, the compounds of the present invention demonstrate significant receptor occupancy of VLA-4 bearing cells after oral administration and are suitable for once-, twice-, or thrice-a-day oral administration. This invention also relates to compositions containing such compounds and methods of treatment using such compounds.

DETAILED DESCRIPTION OF THE INVENTION

The present invention provides a compound of formula I:

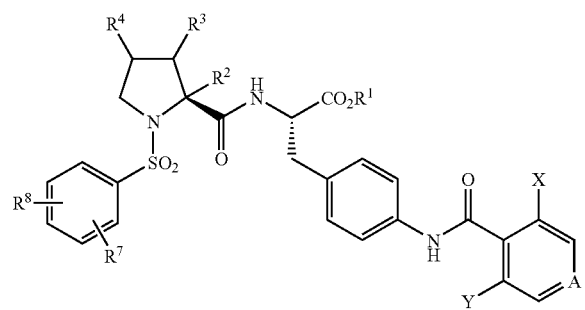

I or a pharmaceutically acceptable salt thereof, wherein:

A is N or $N^+$—$O^+$;

X and Y are independently selected from halogen, $C_{1-3}$alkyl, and $C_{1-3}$alkoxy;

$R^1$ is selected from (1) hydrogen, (2) $C_{1-10}$alkyl, (3) -($C_{1-10}$alkyl)-aryl, (4) -($C_{1-10}$alkyl)-O—$C_{1-10}$alkyl, (5) -($C_{1-10}$alkyl)-OC(O)-$C_{1-10}$alkyl, (6) -($C_{1-10}$alkyl)-OC(O)-aryl, (7) -($C_{1-10}$alkyl)-OC(O)O—$C_{1-10}$alkyl, and (8) -($C_{1-10}$alkyl)-$N^+(C_{1-3}$alkyl$)_3$; wherein alkyl is optionally substituted with one to three substituents independently selected from $R^a$, and aryl is optionally substituted with one to three substituents independently selected from $R^b$;

$R^2$ is hydrogen or methyl;

one of $R^3$ and $R^4$ is hydrogen, and the other is

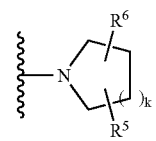

k is 0 to 4;

$R^5$ and $R^6$ are independently selected from hydrogen, fluorine, $CF_3$, and $CO_2R^f$, with the proviso that $R^5$ and $R^6$ are not both hydrogen;

$R^7$ and $R^8$ are independently selected from H, —$SO_2$—$C_{1-3}$alkyl, CN, $CF_3$, $OCF_3$, and halogen;

$R^a$ is selected from (1) —$OR^d$, (2) —$NR^dS(O)_mR^e$, (3) —$NO_2$, (4) halogen, (5) —$S(O)_mR^d$, (6) —$SR^d$, (7) —$S(O)_2OR^d$, (8) —$S(O)_mNR^dR^e$, (9) —$NR^dR^e$, (10) —$O(CR^fR^g)_nNR^dR^e$, (11) —$C(O)R^d$, (12) —$CO_2R^d$, (13) —$CO_2(CR^fR^g)_nCONR^dR^e$, (14) —$OC(O)R^d$, (15) —CN, (16) —$C(O)NR^dR^e$, (17) —$NR^dC(O)R^e$, (18) —$OC(O)NR^dR^e$, (19) —$NR^dC(O)OR^e$, (20) —$NR^dC(O)NR^dR^e$, (21) —$CR^d(N$—$OR^e)$, (22) $CF_3$, (23) —$OCF_3$, (24) $C_{3-8}$cycloalkyl, and (25) heterocyclyl; wherein cycloalkyl and heterocyclyl are optionally substituted with one to three groups independently selected from $R^c$;

$R^b$ is selected from (1) a group selected from $R^a$, (2) $C_{1-10}$alkyl, (3) $C_{2-10}$ alkenyl (4) $C_{2-10}$ alkynyl, (5) aryl, and (6)

-($C_{1-10}$ alkyl)-aryl, wherein alkyl, alkenyl, alkynyl, and aryl are optionally substituted with one to three substituents selected from a group independently selected from $R^c$;

$R^c$ is (1) halogen, (2) amino, (3) carboxy, (4) $C_{1-4}$alkyl, (5) $C_{1-4}$alkoxy, (6) aryl, (7) -($C_{1-4}$alkyl)-aryl, (8) hydroxy, (9) $CF_3$, (10) $OC(O)C_{1-4}$alkyl, (11) $OC(O)NR^fR^g$, or (12) aryloxy;

$R^d$ and $R^e$ are independently selected from hydrogen, $C_{1-10}$alkyl, $C_{2-10}$alkenyl, $C_{2-10}$alkynyl, Cy and -($C_{1-10}$ alkyl)-Cy, wherein alkyl, alkenyl, alkynyl and Cy are optionally substituted with one to four substituents independently selected from $R^c$; or $R^d$ and $R^e$ together with the atom(s) to which they are attached form a heterocyclic ring of 4 to 7 members containing 0-2 additional heteroatoms independently selected from O, S and N—$R^h$;

$R^f$ and $R^g$ are independently selected from hydrogen, $C_{1-10}$alkyl, Cy and -($C_{1-10}$alkyl)-Cy; or $R^f$ and $R^g$ together with the carbon to which they are attached form a ring of 5 to 7 members containing 0-2 heteroatoms independently selected from oxygen, sulfur and nitrogen;

$R^h$ is selected from $R^f$ and —$C(O)R^f$;

Cy is selected from cycloalkyl, heterocyclyl, aryl, and heteroaryl;

m is 1 or 2; and n is 2 to 5.

In one subset of formula I are compounds wherein one of X and Y is halogen and the other is selected from halogen, $C_{1-3}$alkyl and $C_{1-3}$alkoxy. In one embodiment thereof X and Y are each halogen, preferably each is chlorine.

In another subset of formula I are compounds wherein $R^1$ is hydrogen, $C_{1-4}$alkyl, -($C_{1-4}$alkyl)$OC_{1-4}$alkyl, or -($C_{1-4}$ alkyl)$N^+(C_{1-3}$alkyl)$_3$. In one embodiment $R^1$ is selected from hydrogen, methyl, ethyl, 2-methoxyethyl, and 2-(trimethylaininium)ethyl.

In a third subset of formula I are compounds wherein one of $R^3$ and $R^4$ is hydrogen, and the other is selected from

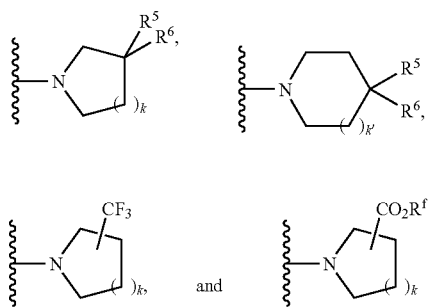

wherein one of $R^5$ and $R^6$ is F and the other is H or F, k is 0 to 4, and k' is 0 to 2. In one embodiment thereof the non-hydrogen substituent is selected from 3,3-difluoro-1-azetidinyl, 3,3-difluoro-1-pyrrolidinyl, 3,3-difluoro-1-piperidinyl, 3-fluoro-1-azetidinyl, 3-fluoro-1-pyrrolidinyl, 3-fluoro-1-piperidinyl, 4,4-difluoro-1-piperidinyl, 4-fluoro-1-piperidinyl, 2-trifluoromethyl-1-pyrrolidinyl, 2-carboxy-1-pyrrolidinyl, and 2-(t-butoxycarbonyl)-1-pyrrolidinyl.

In a fourth subset of formula I are compounds having the formula Ia:

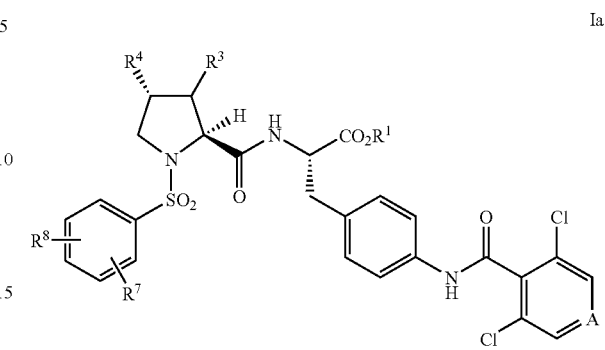

or a pharmaceutically acceptable salt thereof, wherein

A is N or $N^+O^-$;

$R^1$ is selected from hydrogen, $C_{1-10}$alkyl, -($C_{1-4}$alkyl)-aryl, -($C_{1-4}$alkyl)-O—$C_{1-4}$alkyl, and -($C_{1-4}$alkyl)-$N^+(C_{1-3}$alkyl)$_3$;

one of $R^3$ and $R^4$ is hydrogen and the other is selected from

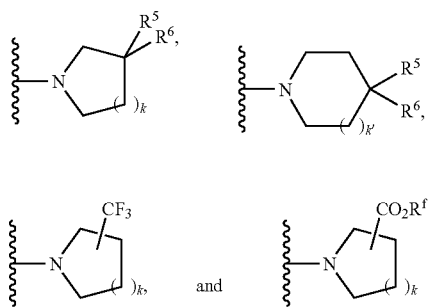

wherein one of $R^5$ and $R^6$ is F and the other is H or F, k is 0 to 4, and k' is 0 to 2; $R^7$ and $R^8$ are independently selected from H, $SO_2$—$C_{1-3}$alkyl, CN, $CF_3$, $OCF_3$, and halogen. Preferably k is 0 to 2.

In one embodiment of formula Ia are compounds wherein $R^3$ is hydrogen and $R^4$ is selected from 3,3-difluoro-1-azetidinyl, 3,3-difluoro-1-pyrrolidinyl, 3,3-difluoro-1-piperidinyl, 3-fluoro-1-azetidinyl, 3-fluoro-1-pyrrolidinyl, 3-fluoro-1-piperidinyl, 4,4-difluoro-1-piperidinyl, 4-fluoro-1-piperidinyl, 2-trifluoromethyl-1-pyrrolidinyl. In a second embodiment of formula Ia are compounds wherein $R^4$ is hydrogen and $R^3$ is selected from 3,3-difluoro-1-azetidinyl, 3,3-difluoro-1-pyrrolidinyl, 3,3-difluoro-1-piperidinyl, 3-fluoro-1-azetidinyl, 3-fluoro-1-pyrrolidinyl, 3-fluoro-1-piperidinyl, 4,4-difluoro-1-piperidinyl, 4-fluoro-1-piperidinyl, 2-trifluoromethyl-1-pyrrolidinyl, 2-carboxy-1-pyrrolidinyl, and 2-(t-butoxycarbonyl)-1-pyrrolidinyl.

In another aspect the present invention provides a method for the prevention or treatment of diseases, disorders, conditions or symptoms mediated by cell adhesion in a mammal which comprises administering to said mammal an effective amount of a compound of formula I or a pharmaceutically acceptable salt thereof. This aspect includes the use of a compound of formula I or a pharmaceutically acceptable salt thereof in the manufacture of a medicament for the treatment of diseases, disorders, conditions or symptoms mediated by cell adhesion in a mammal. In one embodiment said disease or disorder is selected from asthma, allergic rhinitis, multiple sclerosis, atherosclerosis, inflammatory bowel disease, rheumatoid arthritis, organ transplantation, acute leukemia, and sickle cell anemia.

In another aspect the present invention provides a method for preventing the action of VLA-4 in a mammal which comprises administering to said mammal a therapeutically effective amount of a compound of formula I or a pharmaceutically acceptable salt thereof. This aspect includes the use of a compound of formula I in the manufacture of a medicament for preventing the action of VLA-4 in a mammal.

Another aspect of the present invention provides a pharmaceutical composition which comprises a compound of formula I or a pharmaceutically acceptable salt thereof, and a pharmaceutically acceptable carrier.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaplhthyl, decahydronaphthyl, indanyl, and the like.

"Aryl" means mono- or bicyclic aromatic rings containing only carbon atoms. The term also includes aryl group fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms in which the point of attachment may be carbon or nitrogen. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halogen" includes fluorine, chlorine, bromine and iodine.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or EtOAc or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The ability of the compounds of Formula I to antagonize the actions of VLA-4 integrin makes them useful for preventing or reversing the symptoms, disorders or diseases induced by the binding of VLA-4 to its various ligands. Thus, these antagonists will inhibit cell adhesion processes including cell activation, migration, proliferation and differentiation. Accordingly, another aspect of the present invention provides a method for the treatment (including prevention, alleviation, amelioration or suppression) of diseases or disorders or symptoms mediated by VLA-4 binding and cell adhesion and activation, which comprises administering to a mammal an effective amount of a compound of Formula I. Such diseases, disorders, conditions or symptoms are, for example (1) multiple sclerosis, (2) asthma, (3) allergic rhinitis, (4) allergic conjunctivitis, (5) inflammatory lung diseases, (6) rheumatoid arthritis, (7) septic arthritis, (8) type I diabetes, (9) organ transplantation rejection, (10) restenosis, (11) autologous bone marrow transplantation, (12) inflammatory sequelae of viral infections, (13) myocarditis, (14) inflammatory bowel disease including ulcerative colitis and Crohn's disease, (15) certain types of toxic and immune-based nephritis, (16) contact dermal hypersensitivity, (17) psoriasis, (18) tumor metastasis, (19) atherosclerosis, (20) sickle cell anemia, (21) certain acute leukemias, (22) various melanomas, carcinomas and sarcomas (including multiple myeloma); (23) acute respiratory distress syndrome; (24) uveitis; (25) circulatory shock; and (26) hepatitis.

The utilities of the present compounds in these diseases or disorders may be demonstrated in animal disease models that have been reported in the literature. The following are examples of such animal disease models: i) experimental allergic encephalomyelitis, a model of neuronal demyelination resembling multiple sclerosis (for example, see T. Yednock et al., *Nature*, 356, 63 (1993) and E. Keszthelyi et al., *Neurology*, 47, 1053 (1996)); ii) bronchial hyperresponsiveness in sheep and guinea pigs as models for the various phases of asthma (for example, see W. M. Abraham et al., *J. Clin. Invest.* 93, 776 (1993) and A. A. Y. Milne and P. P. Piper, *Eur. J. Pharmacol.*, 282, 243 (1995)); iii) adjuvant-induced arthritis in rats as a model of inflammatory arthritis (see C. Barbadillo et al., *Arthr. Rheuma.* (Suppl.), 36 95 (1993) and D. Seiffge, *J. Rheumatol.*, 23, 12 (1996)); iv) adoptive autoimmune diabetes in the NOD mouse (see J. L. Baron et al., *J. Clin. Invest.*, 93, 1700 (1994), A. Jakubowski et al., *J. Immunol.*, 155, 938 (1995), and X. D. Yang et al., *Diabetes*, 46, 1542 (1997)); v) cardiac allograft survival in mice as a model of organ transplantation (see M. Isobe et al., *Tranplant. Proc.*, 26, 867 (1994) and S. Molossi et al., *J. Clin Invest.*, 95, 2601 (1995)); yl) spontaneous chronic colitis in cotton-top tamarins which resembles human ulcerative colitis, a form of inflammatory bowel disease (see D. K. Podolsky et al., *J. Clin. Invest.*, 92, 372 (1993)); vii) contact hypersensitivity models as a model for skin allergic reactions (see T. A. Ferguson and T. S. Kupper, *J. Immunol.*, 150, 1172 (1993) and P. L. Chisholm et al., *Eur. J. Immunol.*, 2,3 682 (1993)); viii) acute nephrotoxic nephritis (see M. S. Mulligan et al., *J. Clin. Invest.*, 91, 577 (1993)); ix) tumor metastasis (for examples, see M. Edward, *Curr. Opin. Oncol.*, 7, 185 (1995)); x) experimental autoimmune thyroiditis (see R. W. McMurray et al., *Autoimmunity*, 23, 9 (1996); xi) ischemic tissue damage following arterial occlusion in rats (see F. Squadrito et al., *Eur. J. Pharmacol.*, 318, 153 (1996)); xii) inhibition of TH2 T-cell cytokine production including IL-4 and IL-5 by VLA-4 antibodies which would attenuate allergic responses (*J. Clinical Investigation* 100, 3083 (1997); xiii) antibodies to VLA-4 integrin mobilize long term repopulating cells and augment cytokine-induced mobilizationin primates and mice (*Blood*, 90 4779-4788 (1997); xiv) sickle reticulocytes adhere to VCAM-1 (Blood 85 268-274 (1995) and *Blood* 88 4348-4358 (1996); xv) chemokine stromal cell derived factor 1 modulates VLA-4 integrin mediated multiple myeloma cell adhesion to CS-1/fibronectin and VCAM-1 (*Blood*, 97, 346-351 2001)

Dose Ranges

The magnitude of prophylactic or therapeutic dose of a compound of Formula I will, of course, vary with the nature and severity of the condition to be treated, and with the particular compound of Formula I used and its route of administration. The dose will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.01 mg to about 25 mg (preferably from 0.1 mg to about 10 mg) of a compound of Formula I per kg of body weight per day.

In the case where an oral composition is employed, a suitable dosage range is, e.g. from about 0.01 mg to about 100 mg of a compound of Formula I per kg of body weight per day, preferably from about 0.1 mg to about 10 mg per kg.

For use where a composition for sublingual administration is employed, a suitable dosage range is from 0.01 mg to about 25 mg (preferably from 0.1 mg to about 5 mg) of a compound of Formula I per kg of body weight per day.

For the treatment of asthma, a compound of Formula I may be used at a dose of from about 0.1 mg/kg to about 100 mg/kg, preferably from about 1 mg/kg to 10 mg/kg, by oral/inhalation/sublingual/etc. once, twice, three times daily, etc. The dose may be adminstered as a single daily dose or divided for twice or thrice daily administration.

For the treatment of multiple sclerosis, a compound of Formula I may be used at a dose of from about 0.1 mg/kg to about 100 mg/kg, preferably from about 1 mg/kg to 10 mg/kg, by oral/inhalation/sublingual/etc. once, twice, three times daily, etc. The dose may be adminstered as a single daily dose or divided for twice or thrice daily administration.

For the treatment of inflammatory bowel disease, a compound of Formula I may be used at a dose of from about 0.1 mg/kg to about 100 mg/kg, preferably from about 1 mg/kg to 10 mg/kg, by oral/inhalation/etc. once, twice, three times daily, etc. The dose may be adminstered as a single daily dose or divided for twice or thrice daily administration.

For the treatment of rheumatoid arthritis, a compound of Formula I may be used at a dose of from about 0.1 mg/kg to about 100 mg/kg, preferably from about 1 mg/kg to 10 mg/kg, by oral/inhalation/sublingual/etc. once, twice, three times daily, etc. The dose may be adminstered as a single daily dose or divided for twice or thrice daily administration.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, sublingual, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, sublingual, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Inj. Suspension (I.M.) | mg/mL |
|---|---|
| Cmpd of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

| Tablet | mg/tab. |
|---|---|
| Cmpd of Formula I | 25 |
| Microcryst. Cellulose | 415 |
| Povidone | 14.0 |
| Pregelatinized Starch | 43.5 |
| Magnesium Stearate | 2.5 |
| | 500 |

| Capsule | mg/cap. |
|---|---|
| Cmpd of Formula I | 25 |
| Lactose Powder | 573.5 |
| Magnesium Stearate | 1.5 |
| | 600 |

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (a) other VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206, as well as natalizumab; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilainine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, salmeterol and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib, rofecoxib, and parecoxib; (h) inhibitors of phosphodiesterase type IV (PDE-IV); (i) antagonists of the chemokine receptors, especially CCR-1, CCR-2, and CCR-3; (j) cholesterol lowering agents such as HMG-CoA reductase inhibitors (lovastatin, simvastatin, pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguamides (metformin), a-glucosidase inhibitors (acarbose) and glitazones (troglitazone, pioglitazone, englitazone, MCC-555, BRL49653 and the like); (l) preparations of interferon beta (interferon beta-1a, interferon beta-1b); (m) anticholinergic agents such as muscarinic antagonists (ipratropium and tiatropium); (n) current treatments for multiple sclerosis, including prednisolone, glatiramer, deoxyadenosine, mitoxantrone, methotrexate, and cyclophosphamide; (o) p38 kinase inhibitors; (p) other compounds such as 5-aminosalicylic acid and prodrugs thereof, antimetabolites such as azathioprine and 6-mercaptopurine, and cytotoxic cancer chemotherapeutic agents.

The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Abbreviations that may be used in the following Schemes and Examples include: 4-DMAP: 4-dimethylaminopyridine; AcCN: acetonitrile; BOC: tert-butoxycarbonyl; BOC-ON:2-(tert-butoxycarbonyloxyimino)-2-phenylacetonitrile; BOP: benzotriazol-1-yloxy-tris(dimethylamino)-phosphonium hexafluorophosphate; brine: saturated NaCl solution; DIPEA: N,N-diisopropylethylamine; DMF: dimethylformamide; DMSO: dimethylsulfoxide; Et: ethyl; EtOAc: ethyl acetate; EtOH: ethanol; g or gm: gram; h or hr: hours; HATU: O-(7-azabenzotriazol-1-yl)-1,1,3,3-tetramethyluronium hexafluorophosphate; BBTU: O-(benzotriazol-1-yl)-1,1,3,3-tetramethyluronium hexafluorophosphate; HOAc: acetic acid; HOAt: 1-hydroxy-7-azabenzotriazole; HOBt: 1-hydroxybenzotriazole; HPLC: high pressure liquid chromatography; in vacuo: rotoevaporation; Me: methyl; MeOH: methanol; mg: milligram; MHz: megahertz; min: minutes; mL: milliliter; munol: millimole; MS or ms: mass spectrum; MsCl: methanesulfonyl chloride; Ph: phenyl; Ph$_3$P: triphenylphosphine; PyBOP: (benzotriazol-1-yloxy)tripyrrolidinophosphonium hexafluorophosphate; rt: room temperature; TEA: triethylamine; TFA: trifluoroacetic acid; TIF: tetrahydrofuran.

Compounds of the present invention may be prepared by procedures illustrated in the accompanying schemes. In Scheme 1, a substituted pyridyl-4-carboxylic acid derivative A is treated with thionyl chloride to make the carboxylic acid chloride derivative which is then reacted with a 4-amino-(L)-phenylalanine derivative to yield the amide B. The N-BOC-protecting group in B is removed with strong acid (TFA or HCl) to afford the free amine C.

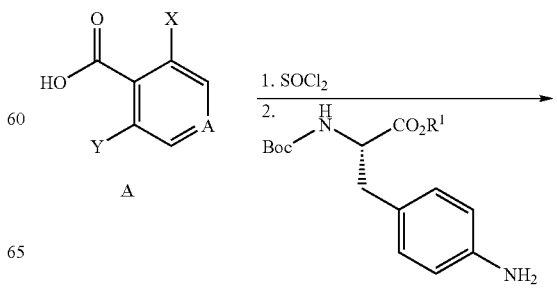

Scheme 1

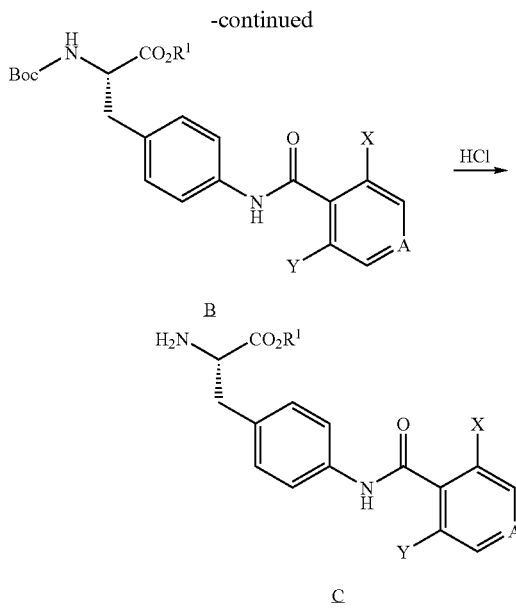

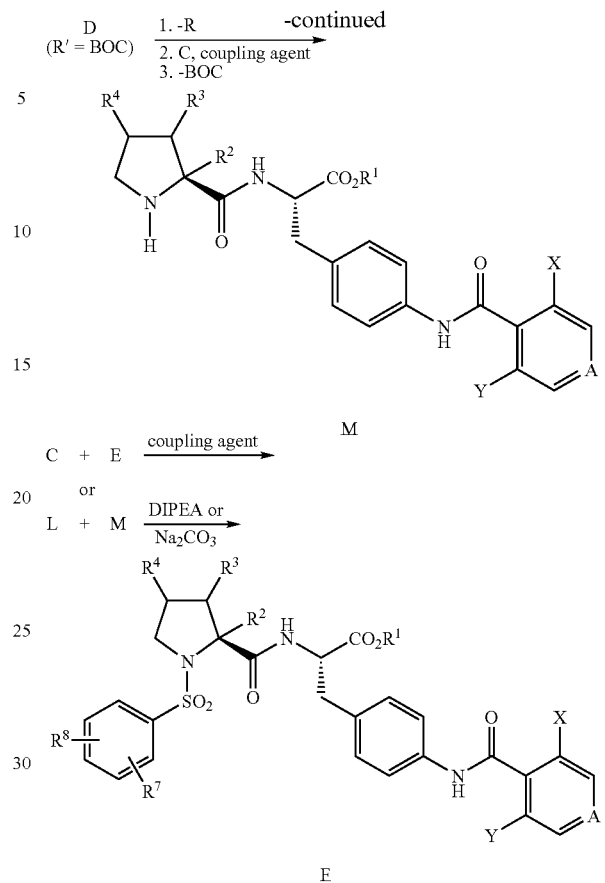

In Scheme 2, an appropriately substituted (L)-proline ester D (R'=H) is sulfonylated with 3-cyanobenzenesulfonyl chloride L in the presence of base (DIPEA or $Na_2CO_3$) to yield sulfonamide E which, if containing an ester protecting group, is treated with hydroxide to afford the free acid. Amine C and acid E are reacted together in the presence of an appropriate coupling agent (eg., PyBOP, HBTU/HOAt, or E may be first converted to the corresponding acid chloride) to afford amide F. Alternatively, the proline ester D (R'=BOC) is hydrolyzed to the corresponding acid by treatment with a base such as LiOH. The acid is then coupled with C, as described above, to give M, following the removal of the BOC group. The amine M is then sulfonylated with L in the presence of a base to provide F. The ester in F can be hydrolyzed with hydroxide (if $R^1$ is n- or i-alkyl) or TFA or HCl (if $R^1$ is tert-butyl) to afford the corresponding acid.

Scheme 2

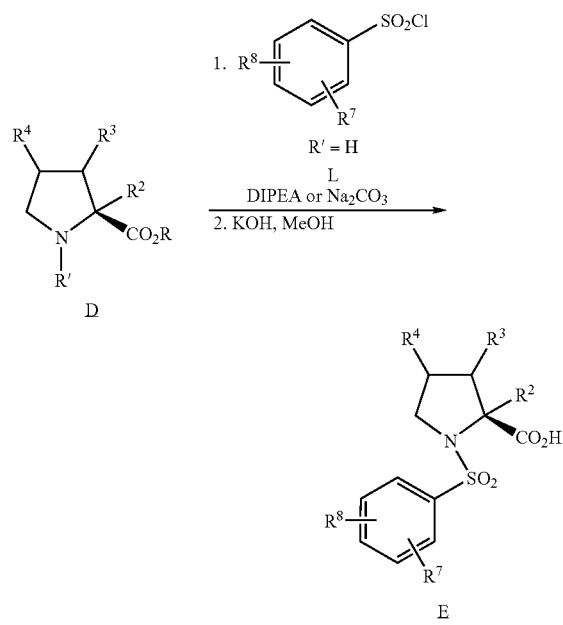

Biological Evaluation

Compounds of formula I are potent antagonists of VLA-4 with significant and sustained receptor occupancy on VLA-4 bearing cells. The rate of dissociation of a test compound from VLA-4 on Jurkat cells may be determined by the method described in G. Doherty et al., *Bioorganic & Medicinal Chemistry Letters*, 13, 1891 (2003). Compounds of the present invention had half-lives of dissociation of greater than three hours ($t_{1/2}>3$ hr) in this assay, demonstrating they are tight binding inhibitors of VLA-4.

VLA-4 receptor occupancy after oral dosing in rats and dogs may be determined by the method described in D. R. Leone et al., *J. Pharmacol. Exper. Therap.*, 305, 1150 (2003). Compounds of the present invention demonstrated sustained and significant receptor occupancy (>50%) after oral dosing.

Compounds of the present invention may be prepared by procedures detailed in the following examples. The examples provided are illustrative of the present invention and are not to be construed as limiting its scope in any manner:

REFERENCE EXAMPLE 1

4-((3',5'-Dichloroisonicotinoyl)amino)-(L)-phenylalanine, Ethyl Ester, HCl

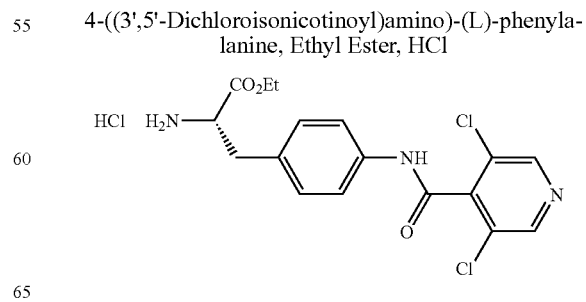

Step A: To 500 mL of absolute ethanol under nitrogen at 0° C. was added thionyl chloride (21 mL, 0.29 mol) over 5 min, and the clear solution was stirred at 0° C. for 10 min and then at rt for 30 min. 4-Nitro-L-phenylalanine (50.2 g, 0.24 mol) was added in one portion, and the mixture was refluxed overnight. The resulting mixture was concentrated in vacuo to give 4-nitro-L-phenylalanine, ethyl ester, HCl (60 g) as a white solid. $^1$H NMR (400 MHz, CD$_3$OD) δ 8.21 (d, 2H), 7.54 (d, 2H), 4.39 (dd, 1H), 4.22 (q, 2H), 3.24-3.40 (m, 2H), 1.22 (t, 3H).

Step B: To a suspension of the compound of Step A (60 g, 0.22 mol) in methylene chloride (1.5 L) under nitrogen was added TEA (31 mL). After stirring at rt for 10 min, di-t-butyl dicarbonate (49 g, 0.22 mol) and 4-DMAP (0.1 g) was added, and the reaction mixture was stirred at rt overnight, washed with 1N HCl (2×200 mL), H$_2$O (2×200 mL) and brine (1×250 mL), dried over anhydrous Na$_2$SO$_4$, filtered and concentrated to afford N-BOC-4-nitro-L-phenylalanine, ethyl ester (78 g). $^1$H NMR (400 MHz, CDCl$_3$) δ 8.14 (d, 2H), 7.28 (d, 2H), 4.30-4.65 (m, 1H), 4.15 (q, 2H), 3.00-3.30 (m, 2H), 1.35 (s, 9H), 1.20 (t, 3H).

Step C: A solution of the compound of Step B (78.3 g, 0.22 mol) in absolute ethanol (300 mL) was purged with nitrogen, and 10% palladium on carbon (1.0 g) was added. After hydrogenated at 40-50 psi for 1 h, the reaction mixture was filtered through Celite, and the cake washed with EtOH followed by EtOAc. The filtrate was concentrated, and the residue was purified by flash column chromatography on silica gel eluting with 4:1 to 1:1 EtOAc/Hexanes to afford N-BOC-4-amino-L-phenylalanine, ethyl ester (60 g). $^1$H NMR (400 MHz, CDCl$_3$) δ 6.90 (d, 2H), 6.63 (d, 2H), 4.20-4.50 (m, 1H), 4.14 (q, 2H), 3.76-3.00 (m, 2H), 1.36 (s, 9H), 1.20 (t, 3H).

Step D: A nitrogen flushed 500 mL round bottom flask was charged with 3,5-dichloroisonicotinic acid (46.5 g, 0.24 mol), CH$_2$Cl$_2$ (150 mL), DMF (0.5 mL), and thionyl chloride (20 mL, 33.9 g 0.28 mol). After the slurry was refluxed for 5 h, additional thionyl chloride (5 mL, 0.70 mol) and CH$_2$Cl$_2$ (100 mL) were added, and the reaction mixture was refluxed for additional 45 min and concentrated, and the residue was azeotroped with toluene to give the crude acyl chloride, which was used immediately. The crude acyl chloride was dissolved in CH$_2$Cl$_2$ (150 mL) and added to the compound of Step C (60 g, 0.20 mol) and 4-methylmorpholine (44 mL, 0.40 mol) in CH$_2$Cl$_2$ (400 mL) at 0° C. over 5 min. After stirring at 0° C. for 1 h, the reaction was quenched with dilute aqueous NaHCO$_3$. The organic layer was separated and the aqueous layer was extracted with CH$_2$Cl$_2$ (500 mL). The organic layers were combined, dried over anhydrous MgSO$_4$ and concentrated in vacuo, and the residue was purified by flash column chromatography on silica gel eluting with 4:1 to 3:2 EtOAc/hexanes to afford N-BOC-4-((3',5'-dichloroisonicotinoyl)amino)-L-phenylalanine, ethyl ester (95 g). $^1$H NMR (400 MHz, CD$_3$OD) δ 8.60 (s, 2H), 7.54 (d, 2H), 7.20 (d, 2H), 4.20-4.36 (m, 1H), 4.10 (q, 2H), 3.02-3.12 (m, 1H), 2.82-2.92 (m, 1H), 1.34/1.30 (s, 9H), 1.20 (t, 3H).

Step E: A solution of the compound of Step D (95 g, 0.197 mol) in EtOAc (1.2 L) was treated with a stream of hydrogen chloride gas over 2 h at rt. The resulting yellow suspension was diluted with hexanes (250 mL), cooled to 0° C. and filtered. The cake washed with hexanes and dried in vacuo to afford the title compound as a yellow solid (80 g). $^1$H NMR (400 MHz, CD$_3$OD) δ 8.64 (s, 2H), 7.66 (d, 2H), 7.30 (d, 2H), 4.28 (dd, 1H), 4.25 (q, 2H), 3.20 (q, 2H), 1.26 (t, 3H).

EXAMPLE 1

N-{N-[(3-Cyanobenzene)sulfonyl]-4(R)-[3,3-difluoropiperidinyl]-(L)-prolyl}-4-[(3',5'-dichloroisonicotinoyl)amino]-(L)-phenylalanine ethyl ester

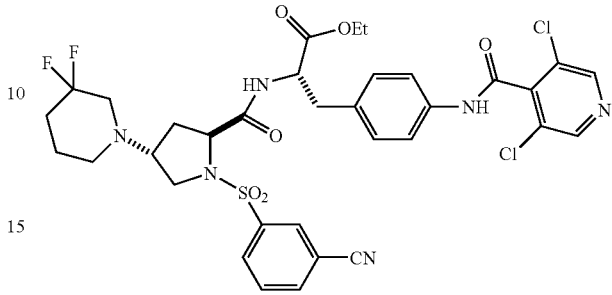

Step 1: Methyl (2S,4S)-1-[(3-cyanophenyl)sulfonyl]-4-hydroxypyrrolidine-2-carboxylate.

To a solution of cis-4-hydroxy-L-proline methyl ester (10.0 g, 68.8 mmol), triethylamine (13.9 g, 138 mmol), and CH$_2$Cl$_2$ (200 mL) was added 3-cyanobenzene-1-sulfonyl chloride (13.9 g, 68.8 mmol). After 1 h, the reaction was partitioned between saturated aqueous NaHCO$_3$ (75 mL) and CH$_2$Cl$_2$ (100 mL). The layers were separated and the aqueous layer was extracted with CH$_2$Cl$_2$ (3×75 mL). The combined organic layers were dried (MgSO$_4$), filtered, and concentrated. The residue was purified on silica gel (1:99→30:70 ethyl acetate-hexanes) to afford the title compound as a colorless crystalline solid: $^1$H NMR (500 MHz, CDCl$_3$) δ 8.19-8.18 (m, 1H), 8.13-8.11 (m, 1H), 7.89-7.85 (m, 1H), 7.69-7.65 (t, 1H), 4.52-4.50 (m, 1H), 4.44-4.43 (m, 1H), 3.67 (s, 3H), 3.52 (dd, 1H), 3.47-3.41 (m, 1H), 3.1 (d, 1H), 2.33-2.27 (m, 1H), 2.20-2.17 (m, 1H); LRMS (ESI) m/z 311 (311 calcd for C$_{13}$H$_{14}$N$_2$O$_5$S, M+H).

Step 2: Methyl (2S,4R)-1-[(3-cyanophenyl)sulfonyl]-4-(3,3-difluoropipendin-1-yl)pyrrolidine-2-carboxylate.

To a solution of the compound of Step 1 (19.6 g, 63.2 mmol), diisopropylethylamine (16.5 g, 127 mmol), and CH$_2$Cl$_2$ (200 mL) was added trifluoromethanesulfonic anhydride (17.8 g, 63.2 mmol) via syringe pump at −60° C. over 30 minutes. The resulting solution was then warmed to −20° C. over 1.5 h, whereupon diisopropylethylamine (5.5 g, 42.5 mmol) was added followed by 3,3-difluoropiperidine hydrochloride (6.67 g, 42.5 mmol). The mixture was then slowly warmed to rt over 5 h. After 12 h at rt, the reaction was partitioned between H$_2$O (150 mL) and CH$_2$Cl$_2$ (100 mL). The layers were separated and the aqueous layer was extracted with CH$_2$Cl$_2$ (3×100 mL). The combined organic layers were dried (MgSO$_4$), filtered, and concentrated. The residue was purified on silica gel (1:99→99:1 ethyl acetate-hexanes) to afford the title compound as a colorless foam: $^1$H NMR (500 MHz, CDCl$_3$) δ 8.16 (s, 1H), 8.10 (d, 1H), 7.88 (d, 1H), 7.68 (t, 1H), 4.48-4.59 (m, 1H), 3.73 (s, 3H), 3.68-3.65 (m, 1H), 3.22-3.17 (m, 2H), 2.64 (br q, 1H), 2.51 (br q, 1H), 2.42-2.41 (m, 2H), 2.23-2.20 (m, 1H), 2.13-2.04 (m, 1H), 1.90-1.82 (m, 2H), 1.74-1.72 (m, 2H); LRMS (ESI) m/z 414 (414 calcd for C$_{18}$H$_{21}$F$_2$N$_3$O$_4$S, M+H).

Step 3: N-{N-[(3-Cyanobenzene)sulfonyl]-4(R)-[3,3-difluoropiperidinyl]-(L)-prolyl}-4-[(3',5'-dichloro isonicotinoyl) amino]-(L)-phenylalanine ethyl ester.

LiOH monohydrate (1.54 g, 64.4 mmol) was added to a solution of the compound of Step 2 (13.3 g, 32.2 mmol), CH$_3$CN (80 mL), and H$_2$O (40 mL) at rt. After 2 h, a H$_2$O solution of HCl (65 mL, 65 mmol, 1 N) was added and the solution was partitioned between ethyl acetate. The layers were separated and the aqueous layer was extracted with ethyl acetate (6×100 mL). The combined organic layers were dried (MgSO$_4$), filtered, and concentrated. The resulting residue was used in the next step without further purification: LRMS (ESI) m/z 400 (400 calcd for C$_{17}$H$_{19}$F$_2$N$_3$O$_4$S, M+H).

Triethylamine (16.4 g, 161 mmol) was added dropwise to a mixture of residue from above (12.8 g, 32.2 mmol), compound of Reference Example 1 (13.4 g, 32.2 mmol), N-(3-dimethylaminopropyl)-N'-ethylcarbodiimide hydrochloride (12.3 g, 64.4 mmol), 1-hydroxybenzotriazole hydrate (8.7 g, 64.4 mmol), and DMF (140 mL) at rt. After 12 h, the reaction was partitioned between H$_2$O (500 mL) and ethyl acetate (200 mL). The layers were separated and the aqueous layer was extracted with ethyl acetate (3×200 mL). The combined organic layers were washed with brine (1×150 mL), dried (MgSO$_4$), filtered, and concentrated. The residue was purified on silica gel (5:95→99:1 ethyl acetatehexanes) to afford the title compound as a colorless foam: $^1$H NMR (500 MHz, CD$_3$OD) δ 8.66 (s, 2H), 8.22-8.21 (m, 1H), 8.06-8.03 (m, 2H), 7.77 (t, 1H), 7.67-7.64 (m, 2H), 7.35-7.32 (m, 2H), 4.74-4.71 (m, 1H), 4.36-4.34 (m, 1H), 4.22 (q, 2H), 3.70-3.67 (m, 1H), 3.25-3.22 (dd, 1H), 3.11-2.95 (m, 3H), 2.64-2.48 (m,2H), 2.40-2.38 (m, 2H), 2.10-2.04 (m, 1H), 1.9-1.65 (m, 5H), 1.28 (t, 3H); LRMS (ESI) m/z 763 (763 calcd for C$_{34}$H$_{34}$Cl$_2$F$_2$N$_6$O$_6$S, M+H).

EXAMPLE 2

N-{N-[(3-Cyanobenzene)sulfonyl]-4(R)-[3,3-d]fluoropiperidinyl-(L)-prolyl}-4-[(3',5'-dichloroisonicotinoyl)amino]-(L)-phenylalanine Lithium hydroxide monohydrate (126 mg, 5.24 mmol) was added to a solution of the compound of Example 1 (1.90 g, 2.62 mmol), CH$_3$CN (13 mL), and H$_2$O (7 mL) at rt. After 2 h, a H$_2$O solution of HCl (5.3 mL, 5.3 mmol, 1 N) was added and the solution was partitioned between ethyl acetate (20 mL). The layers were separated and the aqueous layer was extracted with ethyl acetate (6×20 mL). The combined organic layers were dried (MgSO$_4$), filtered, and concentrated. The residue was purified on silica gel (1:99→20:80 methanol-CH$_2$Cl$_2$) to afford the title compound as a colorless foam:

$^1$H NMR (500 MHz, CD$_3$OD) δ 8.65 (s, 2H), 8.22 (s, 1H), 8.04 (d, 2H), 7.76 (t, 1H), 7.65 (d, 2H), 7.35 (d, 2H), 4.73-4.70 (m, 1H), 4.38-4.35 (m, 1H), 3.71-3.68 (m, 1H), 3.33-3.29 (dd, 1H), 3.11-2.95 (m, 3H), 2.65-2.50 (m, 1H), 2.40-2.39 (m, 2H), 2.11-2.10 (m, 1H), 1.86-1.60 (m, 5H); LRMS (ESI) m/z 735 (735 calcd for C$_{32}$H$_{30}$Cl$_2$F$_2$N$_6$O$_6$S, M+H).

EXAMPLE 3

N-{N-[(3-Cyanobenzene)sulfonyl]-4(R)-[3,3-difluoroazetidin-1-yl]-(L)-prolyl}-4-[(3',5'-dichloroisonicotinoyl)amino]-(L)-phenylalanine ethyl ester

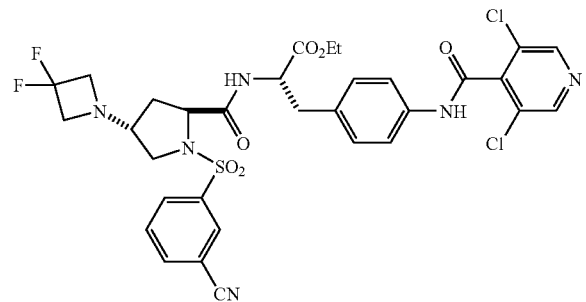

Utilizing the general procedure outlined in Example 1, Steps 2-3, 3,3-difluoropiperidine hydrochloride was exchanged for 3,3-difluoroazetidine hydrochloride to afford the title compound after preparative reverse phase HPLC purification (Phenomenex Synergi 4u Max-RP 80A, 100× 20.2 mm, 20:80→100:0 acetonitrile-water 0.01% TFA) colorless foam: $^1$H NMR (500 MHz, CD$_3$OD) δ 8.65 (s, 2H), 8.21 (s, 1H), 8.04-8.01 (m, 2H), 7.75 (t, 1H), 7.65 (app d, 2H), 7.36 (app d, 2H), 4.74-4.72 (m, 1H), 4.34 (t, 1H), 4.20 (q, 2H), 3.61-3.44 (m, 5H), 3.33-3.10 (m, 4H), 2.05-2.01 (m, 1H), 1.92-1.88 (m, 1H), 1.26 (t, 3H); LRMS (ESI) m/z 735 (735 calcd for C$_{32}$H$_{31}$Cl$_2$F$_2$N$_6$O$_6$S, M+H).

EXAMPLE 4

N-{N-[(3-Cyanobenzene)sulfonyl]-4(R)-[3,3-difluoroazetidin-1-yl]-(L)-prolyl}-4-[(3',5'-dichloroisonicotinoyl)amino]-(L)-phenylalanine Utilizing the general procedure outlined in Example 2, the compound of Example 3 was converted to the title compound after preparative reverse phase HPLC purification (Phenomenex Synergi 4u Max-RP 80A, 100×20.2 mm, 20:80→100:0 acetonitrile-water 0.01% TFA) colorless foam: $^1$H NMR (500 MHz, CD$_3$OD) δ 8.65 (s, 2H), 8.20 (s, 1H), 8.04-7.97 (m, 2H), 7.74(t, 1H), 7.65 (d, 2H), 7.39 (d, 2H), 4.74-4.71 (m, 1H), 4.37 (t, 1H), 3.68-3.62 (m, 2H), 3.55-3.48 (m, 3H), 3.32-3.20 (m, 4H), 3.11-3.04 (m, 1H), 2.07-1.91 (m, 2H); LRMS (ESI) m/z 707 (707 calcd for C$_{30}$H$_{27}$Cl$_2$F$_2$N$_6$O$_6$S, M+H).

EXAMPLE 5

N-{N-[(3-Cyanobenzene)sulfonyl]-4(R)-[3,3-difluoropyrrolidine]-(L)-prolyl}-4-[(3',5'-dichloroisonicotinoyl)amino]-(L)-phenylalanine ethyl ester

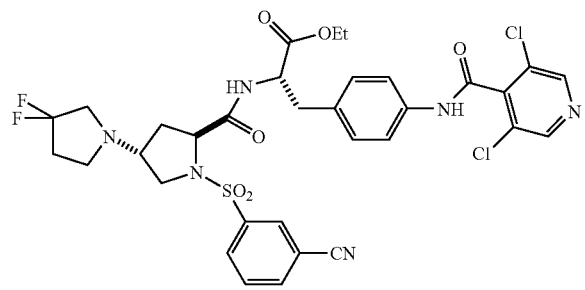

Utilizing the general procedure outlined in Example 1, Steps 2-3, 3,3-difluoropiperidine hydrochloride was exchanged for 3,3-difluoropyrrolidine hydrochloride to afford the title compound as a colorless foam: $^1$H NMR (500 MHz, CD$_3$OD) δ 8.64 (s, 2H), 8.25-8.24 (m, 1H), 8.10-8.07 (m, 1H), 8.04-8.02 (m, 1H), 7.77 (t, 1H), 7.67-7.64 (m, 2H), 7.35-7.32 (m, 2H), 4.78-4.75 (m, 1H), 4.34-4.31 (m, 1H), 4.21 (q, 2H), 3.61-3.59 (m, 1H), 3.29-3.24 (m, 2H), 3.11 (m, 1H), 2.89-2.80 (m, 3H), 2.60-2.58 (m, 2H), 2.04-1.95 (m, 4H), 1.28 (t, 3H); LRMS (ESI) m/z 749 (749 calcd for C$_{33}$H$_{32}$Cl$_2$F$_2$N$_6$O$_6$S, M+H).

EXAMPLE 6

N-{N-[(3-Cyanobenzene)sulfonyl]-4(R)-[3,3-difluoropyrrolidine]-(L)-prolyl}-4-[(3',5'-dichloroisonicotinoyl)amino]-(L)-phenylalanine Utilizing the general procedure outlined in Example 2, the compound of Example 5 was converted to the title compound as a white solid: $^1$H NMR (500 MHz, CD$_3$OD) δ 8.52 (s, 2H), 8.13 (m, 1H), 7.98-7.97 (m, 1H), 7.90-7.88 (m, 1H), 7.65 (t, 1H), 7.50 (d, 2H), 7.24 (d, 2H), 4.54 (m, 1H), 4.20-4.17 (m, 1H), 3.47-3.44 (m, 1H), 3.22-3.20 (m, 1H), 3.13-3.10 (m, 1H), 3.04-3.02 (m, 1H), 2.73-2.67 (m, 3H), 2.50-2.47 (m, 2H), 1.95-1.82 (m, 4H); LRMS (ES) m/z 721 (721 calcd for $C_{31}H_{28}Cl_2F_2N_6O_6S$, M+H).

EXAMPLE 7

N-{N-[(3-Cyanobenzene)sulfonyl]-4(R)-[3,3-difluoropyrrolidine]-(L)-prolyl}-4-[(3',5'-dichloroisonicotinoyl)amino]-(L)-phenylalanine methyl ester

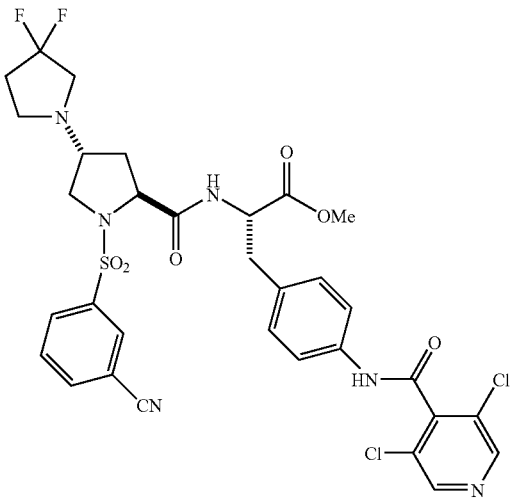

To a solution of the compound of Example 6 (50 mg, 0.07 mmol) in anhydrous methanol (1 mL) was added trimethylsilyldiazomethane (2 M in ether) at 0° C. until a yellow color persisted. After stirring at room temperature for 15 min, the mixture was concentrated to dryness to afford the title compound as a colorless foam: $^1$H NMR (500 MHz, CD$_3$OD) δ 8.64 (s, 2H), 8.21 (m, 1H), 8.06-8.04 (m, 1H), 8.02-8.00 (m, 1H), 7.77 (t, 1H), 7.63-7.61 (m, 2H), 7.23-7.21 (m, 2H), 4.76 (m, 1H), 4.30-4.29 (m, 1H), 3.74 (a, 3H), 3.58-3.57 (m, 1H), 3.28-3.24 (m, 2H), 3.10-3.08 (m, 1H), 2.87-57 (m,5H), 2.04-1.92 (m, 4H); LRMS (ESI) m/z 735 (735 calcd for $C_{32}H_{30}Cl_2F_2N_6O_6S$, M+H).

EXAMPLE 8

N-{N-[(3-Cyanobenzene)sulfonyl]-4(S)-[3,3-difluoropyrrolidine]-(L)-prolyl}-4-[(3',5'-dichloroisonicotinoyl)amino]-(L)-phenylalanine ethyl ester

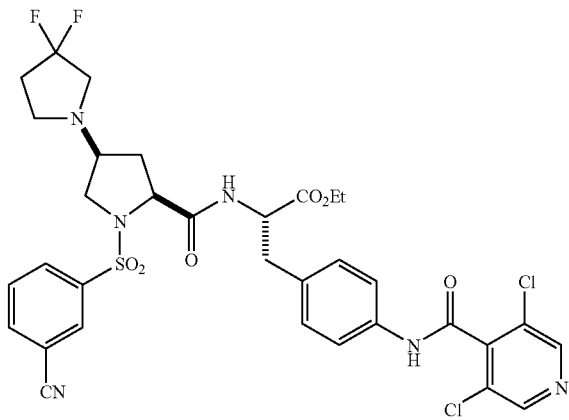

Utilizing the general procedure outlined in Example 1, cis-4-hydroxy-L-proline methyl ester was exchanged for trans-4-hydroxy-L-proline methyl ester to afford the title compound as a colorless foam: LRMS (ESI) m/z 749 (749 calcd for $C_{33}H_{33}Cl_2F_2N_6O_6S$, M+H).

EXAMPLE 9

N-{N-[(3-Cyanobenzene)sulfonyl]-4(S)-[3,3-difluoropyrrolidine]-(L)-prolyl}-4-[(3',5'-dichloroisonicotinoyl)amino]-(L)-phenylalanine Utilizing the general procedure outlined in Example 2, the title compound was obtained from the compound of Example 8 after preparative reverse phase HPLC purification (Phenomenex Synergi 4u Max-RP 80A, 100×20.2 mm, 20:80→100:0 acetonitrile-water 0.01% TFA) colorless foam: $^1$H NMR (500 MHz, CD$_3$OD) δ 8.65 (s, 2H), 8.24 (s, 1H), 8.09-8.03 (m, 2H), 7.77 (t, 1H), 7.36 (d, 2H), 7.37 (d, 2H), 4.73-4.69 (m, 1H), 4.41-4.38 (m, 1H), 3.75-3.40 (m, 7H), 3.30-3.25 (m, 2H), 3.10 (dd, 1H), 2.55-2.48 (m, 3H), 2.28-2.21 (m, 1H); LRMS (ESI) m/z 721 (721 calcd for $C_{31}H_{29}Cl_2F_2N_6O_6S$, M+H).

EXAMPLE 10

N-{N-[(3-Cyanobenzene)sulfonyl]-4(R)-[4,4-difluoropiperidinyl]-(L)-prolyl}-4-[(3',5'-dichloroisonicotinoyl)amino]-(L)-phenylalanine ethyl ester

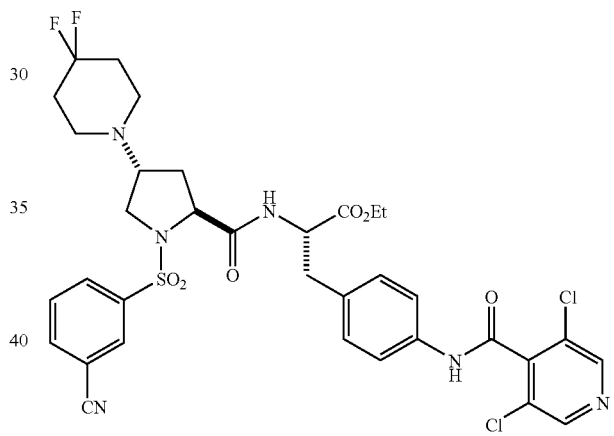

Utilizing the general procedure outlined in Example 1, Steps 2-3, 3,3-difluoropiperidine hydrochloride was exchanged for 4,4-difluoropiperidine hydrochloride to afford the title compound as a colorless foam: $^1$H NMR (500 MHz, CDCl$_3$) δ 8.56 (s, 2H), 8.13 (s, 1H), 8.06 (d, 1H), 7.91 (d, 1H) 7.70 (t, 1H), 7.64 (br s, 1H), 7.54 (d, 2H), 7.20 (d, 2H), 7.06 (br d, 1H), 4.83-4.81 (m, 1H), 4.25 (q, 2H), 4.17 (d, 1H), 3.64-3.61 (m, 1H), 3.26 (dd, 1H), 3.10 (dd, 1H), 2.90 (t, 1H), 2.80-2.70 (m, 1H), 2.48-2.39 (m, 4H), 2.31-2.25 (dd, 1H), 1.94-1.83 (m, 1H), 1.59-1.51 (m, 1H), 1.32 (t, 3H); LRMS (ESI) m/z 763 (763 calcd for $C_{34}H_{35}Cl_2F_2N_6O_6S$, M+H).

EXAMPLE 11

N-{N-[(3-Cyanobenzene)sulfonyl]-4(R)-[4,4-difluoropiperidinyl]-(L)-prolyl}-4-[(3',5'-dichloroisonicotinoyl)amino]-(L)-phenylalanine Utilizing the general procedure outlined in Example 2, the title compound was obtained from the compound of Example 10 as a colorless foam: $^1$H NMR (500 MHz, CD$_3$OD) δ 8.64 (s, 2H), 8.23 (s, 1H), 8.04-8.02 (m, 2H), 7.75 (t, 1H), 7.63 (d, 2H), 7.34 (d, 2H), 4.70-4.67 (m, 1H), 4.40 (d, 1H), 3.73-3.72 (m, 1H), 3.30 (dd, 1H), 3.28-3.05 (m, 3H), 2.58-2.54 (m, 4H), 2.13-2.12 (m, 1H), 1.95-1.80 (m, 5H); LRMS (ESI) m/z 735 (735 calcd for $C_{32}H_{31}Cl_2F_2N_6O_6S$, M+H).

EXAMPLE 12

N-{N-[(3-Cyanobenzene)sulfonyl]-4(R)-[3-3-difluoropiperidinyl]-(L)-prolyl}-4-[(3',5'-dichloroisonicotinoyl)amino]-(L)-phenylalanine-2-methoxyethyl ester

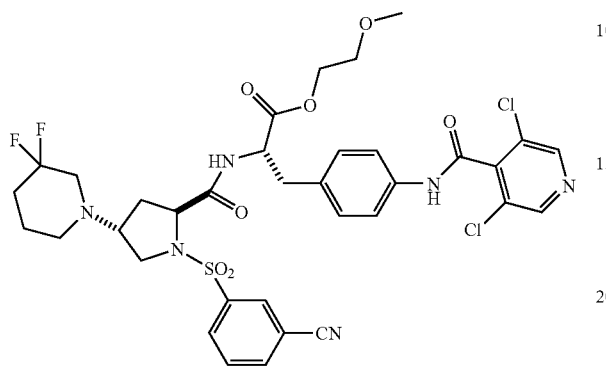

Potassium carbonate (33.0 mg, 0.24 mmol) was added to a solution of the compound of Example 2 (60.0 mg, 0.08 mmol), 1-bromo-2-methoxyethane (22.0 mg, 0.16 mmol), and DMF (1.5 mL). After 24 h, trifluoroacetic acid (45.6 mg, 0.40 mmol) was added and the mixture was directly purified by preparative reverse phase HPLC purification (Phenomenex Synergi 4u Max-RP 80A, 100×20.2 mm, 20:80→100:0 acetonitrile-water 0.01% TFA) to afford the title compound as a colorless foam: $^1$H NMR (500 MHz, CD$_3$OD) δ 8.64 (s, 2H), 8.49 (br d, 1H), 8.17 (s, 1H), 8.02 (d, 1H), 7.93 (d, 1H), 7.71 (t, 1H), 7.65 (d, 2H), 7.35 (d, 2H), 4.68-4.60 (m, 1H), 4.49 (d, 1H), 4.30-4.20 (m, 2H), 3.82 (dd, 1H), 3.67-3.60 (m, 3H), 3.34 (s, 3H), 3.32-3.30 (m, 1H), 3.28 (dd, 1H), 3.20-3.13 (m, 1H), 3.03-3.10 (dd, 1H), 2.95-2.90 (m, 2H), 2.27 (dd, 1H), 2.08-1.96 (m, 3H), 1.90-1.80 (m, 2H); LRMS (ESI) m/z 793 (793 calcd for $C_{35}H_{37}Cl_2F_2N_6O_7S$, M+H).

EXAMPLE 13

N-{N-[(3-Cyanobenzene)sulfonyl]-4(R)-[3,3-difluoropiperdinyl]-(L)-prolyl}-4-[3',5-dichloroisonicotinoyl)amino]-(L)-phenylalanine-choline ester

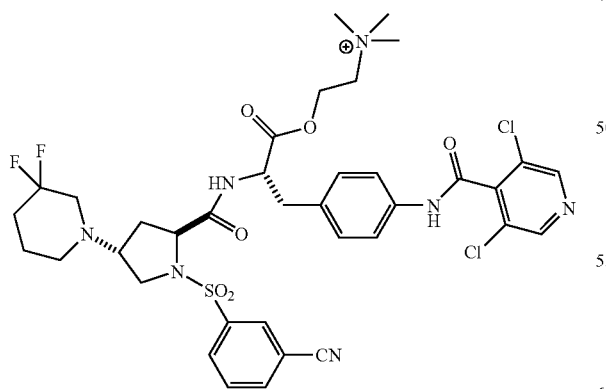

Utilizing the general procedure outlined in Example 12, 1-bromo-2-methoxyethane was exchanged for 2-bromo-N,N,N-trimethylethanaminium bromide to afford the title compound as a colorless foam: $^1$H NMR (500 MHz, CD$_3$OD) δ 8.64 (s, 2H), 8.60 (br d, 1H), 8.23 (s, 1H), 8.09 (d, 1H), 8.05 (d, 1H), 7.79 (t, 1H), 7.62 (d, 2H), 7.34 (d, 2H), 4.75-4.70 (m, 1H), 4.65-4.52 (m, 2H), 4.33-4.31 (m, 1H), 3.80-3.70 (m, 1H), 3.78-3.66 (m, 2H), 3.30 (dd, 1H), 3.16-3.10 (m, 13H), 2.80-2.68 (m, 2H), 2.54-2.52 (m, 2H), 1.91-1.80 (m, 4H), 1.65-1.70 (m, 2H); LRMS (ESI) m/z 820 (820 calcd for $C_{37}H_{42}Cl_2F_2N_7O_6S+$, M+).

EXAMPLE 14

N-{N-[(3-Cyanobenzene)sulfonyl]-4(R)-[3,3-difluoropyrrolidine]-(L)-prolyl}-4-[(3',5'-dichloroisonicotinoyl)amino]-(L)-phenylalanine choline ester

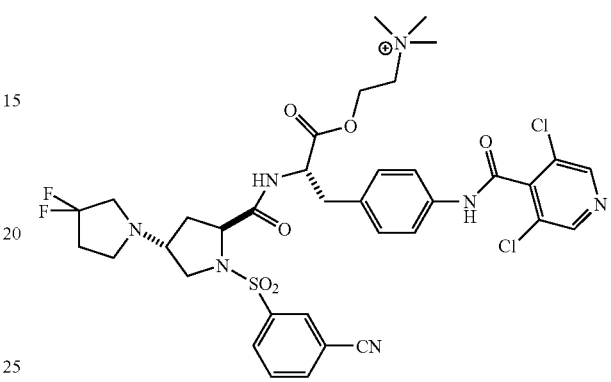

Utilizing the general procedure outlined in Example 12, using the compound of Example 6 and 2-bromo-N,N,N-trimethylethanaminium bromide, the title compound was obtained after preparative reverse phase HPLC purification (Phenomenex Synergi 4u Max-RP 80A, 100×20.2 mm, 20:80→100:0 acetonitrile-water 0.01% TFA) as a colorless foam: $^1$H NMR (500 MHz, CD$_3$OD) δ 8.65 (s, 2H), 8.28-8.25 (m, 1H), 8.14-8.12 (m, 1H), 8.06-8.04 (m, 1H), 7.80-7.77 (t, 1H), 7.64-7.60 (m, 2H), 7.34-7.32 (m, 2H), 4.79-4.75 (m, 1H), 4.65-4.50 (m, 2H), 4.24-4.22 (m, 1H), 3.70-3.61 (m, 3H), 3.57-3.14 (m, 12H), 2.87-2.55 (m, 5H), 2.10-1.95 (m,3H), 1.80-1.78 (m, 1H); LRMS (ESI) m/z 806 (806 calcd for $C_{36}H_{40}Cl_2F_2N_7O_6S+$, M+).

EXAMPLE 15

N-{N-[(3,5-Difluorobenzene)sulfonyl]-4(R)-[3,3-difluoropyrrolidine]-(L)-prolyl}-4-[(3',5'-dichloroisonicotinoyl)amino]-(L)-phenylalanine ethyl ester

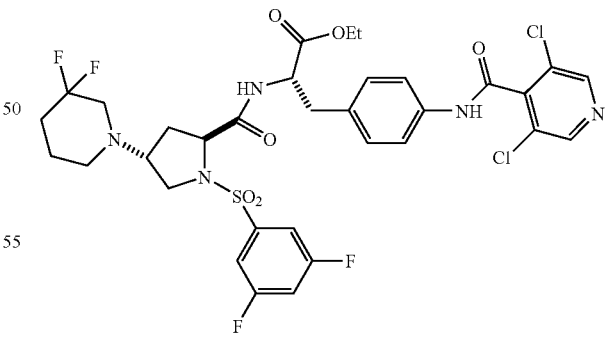

Utilizing the general procedure outlined in Example 1, Steps 1-3,3-cyanobenzene-1-sulfonyl chloride was exchanged for 3,5-difluorobenzene-1-sulfonyl chloride to afford title compound as a colorless foam: $^1$H NMR (500 MHz, CD$_3$OD) δ 8.62 (s, 2H), 7.63-7.61 (m, 2H), 7.48-7.45 (m, 2H), 7.36-7.29 (m, 3H), 4.73-4.70 (m, 1H), 4.32-4.30 (m, 1H), 4.22-4.17 (q, 2H), 3.72-3.70 (m, 1H), 3.23-3.22 (m, 1H), 3.10-3.04 (m, 2H), 3.00-2.94 (m, 1H), 2.61-2.50 (m, 2H), 2.38 (m, 2H), 2.10-2.05 (m, 1H), 1.83-1.77 (m, 3H), 1.65 (m, 2H), 1.28-1.25 (t, 3H); LRMS (ESI) m/z 774 (774 calcd for $C_{33}H_{33}Cl_2F_4N_5O_6S$, M+H).

EXAMPLE 16

N-{N-[(3,5-Difluorobenzene)sulfonyl]-4(R)-[3,3-difluoropyrrolidine]-(L)-prolyl}-4-[(3',5'-dichloroisonicotinoyl)amino]-(L)-phenylalanine Utilizing the general procedure outlined in Example 2, the title compound was obtained from the compound of Example 15 after preparative reverse phase HPLC purification (Phenomenex Synergi 4u Max-RP 80A, 100×20.2 mm, 20:80→100:0 acetonitrile-water 0.01% TFA) as a white solid: $^1$H NMR (500 MHz, CD$_3$OD) δ 8.64 (s, 2H), 7.63-7.62 (d, 2H), 7.43-7.31 (m, 5H), 4.64-4.60 (m, 2H), 4.20-4.14 (m, 1H), 4.00-3.96 (m, 1H), 3.72-3.56 (m, 3H), 3.46-3.01 (m, 4H), 2.50-2.06 (m, 6H); LRMS (ESI) m/z 746 (746 calcd for $C_{31}H_{29}Cl_2F_4N_5O_6S$, M+H).

EXAMPLE 17

N-{N-[(3-Cyanobenzene)sulfonyl]-4(R)-[2(S)-(trifluoromethyl)pyrrolidine]-(L)-prolyl}-4-[(3',5'-dichloroisonicotinoyl)amino]-(L)-phenylalanine ethyl ester

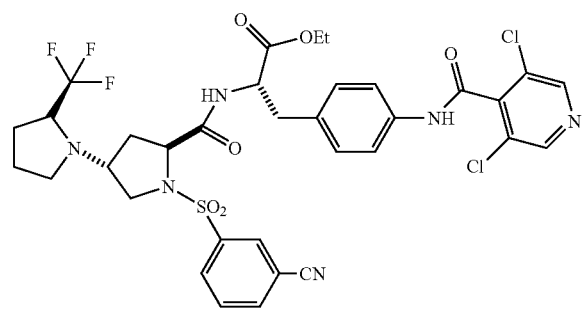

Utilizing the general procedure outlined in Example 1, Steps 2-3, 3,3-difluoropiperidine hydrochloride was exchanged for 2(S)-(trifluoromethyl)pyrrolidine to afford the title compound as a white solid: $^1$H NMR (500 MHz, CD$_3$OD) δ 8.64 (s, 2H), 8.17 (m, 1H), 8.03-8.00 (m, 2H), 7.77-7.74 (t, 1H), 7.63-7.62 (d, 2H), 7.32-7.30 (d, 2H), 4.72-4.70 (m, 1H), 4.35-4.32 (m, 1H), 4.22-4.18 (q, 2H), 3.62-3.60 (m, 1H), 3.48-3.42 (m, 1H), 3.35-3.30 (m, 2H), 3.09-3.01 (m, 2H), 2.88-2.73 (m, 1H), 2.52-2.44 (m, 1H), 2.00-1.80 (m, 4H), 1.76-1.74 (m, 2H), 1.28-1.25 (t, 3H); LRMS (ESI) m/z 781 (781 calcd for $C_{34}H_{33}Cl_2F_3N_6O_6S$, M+H).

EXAMPLE 18

N-{N-[(3-Cyanobenzene)sulfonyl]-4(R)-[2(S)-(trifluoromethyl)pyrrolidine]-(L)-prolyl}-4-[(3',5'-dichloroisonicotinoyl)amino]-(L)-phenylalanine Utilizing the general procedure outlined in Example 2, the title compound was obtained from the compound of Example 17 as an off-white solid: $^1$H NMR (500 MHz, CD$_3$OD) δ 8.65 (s, 2H), 8.21 (s, 1H), 8.04-8.02 (m, 2H), 7.79-7.76 (t, 1H), 7.66-7.64 (d, 2H), 7.36-7.34 (d, 2H), 4.74-4.72 (m, 1H), 4.39-4.37 (m, 1H), 3.64-3.61 (m, 1H), 3.53-3.45 (m, 1H), 3.33-3.29 (m, 2H), 3.11-3.05 (m, 2H), 2.90-2.89 (m, 1H), 2.53-2.51 (m, 1H), 2.06-1.78 (m, 6H); LRMS (ESI) m/z 753 (753 calcd for $C_{32}H_{30}Cl_2F_3N_6O_6S$, M+H).

EXAMPLE 19

N-{N-[3-Cyanobenzene)sulfonyl]-4(R)-[2-(trifluoromethyl)pyrrolidine]-(L)-prolyl}-4-[(3',5'-dichloroisonicotinoyl)amino]-(L)-phenylalanine ethyl ester

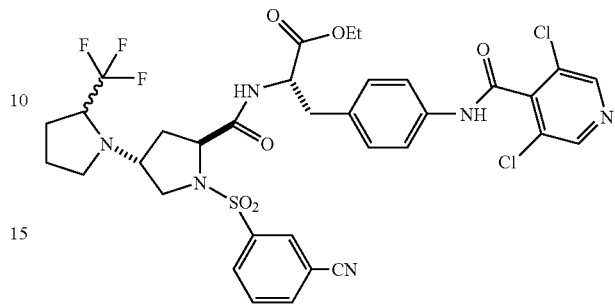

Utilizing the general procedure outlined in Example 1, Steps 2-3, 3,3-difluoropiperidine hydrochloride was exchanged for 2-(trifluoromethyl)pyrrolidine to afford the title compound, a white solid, as a mixture of diastereomers: $^1$H NMR (500 MHz, CD$_3$OD) δ 8.62 (s, 2H), 8.22-8.18 (m, 1H), 8.05-8.00 (m, 2H), 7.77-7.74 (m, 1H), 7.63-7.62 (m, 2H), 7.32-7.30 (m, 2H), 4.73-4.70 (m, 1H), 4.35-4.33 (m, 1H), 4.22-4.18 (m, 2H), 3.62-3.60 (m, 1H), 3.48-3.22 (m, 3H), 3.09-3.04 (m, 2H), 2.90-2.91 (m, 1H), 2.52-2.44 (m, 1H), 2.00-1.80 (m, 4H), 1.76-1.74 (m, 2H), 1.28-1.25 (m, 3H); LRMS (ESI) m/z 781 (781 calcd for $C_{34}H_{33}Cl_2F_3N_6O_6S$, M+H).

EXAMPLE 20

N-{N-[(3-Cyanobenzene(sulfonyl)]-4(R)-[2-(trifluoromethyl)pyrrolidine]-(L)-prolyl}-4-[(3',5'-dichloroisonicotinoyl)amino]-(L)-phenylalanine Utilizing the general procedure outlined in Example 2, the title compound (as a mixture of diastereomers) was obtained from the compound of Example 19 as an off-white solid,: $^1$H NMR (500 MHz, CD$_3$OD) δ 8.63 (s, 2H), 8.21-8.19 (m, 1H), 8.02-8.00 (m, 2H), 7.76-7.71 (m, 1H), 7.63-7.61 (m, 2H), 7.34-7.31 (d, 2H), 4.71-4.69 (m, 1H), 4.36-4.34 (m, 1H), 3.61-3.58 (m, 1H), 3.34-3.27 (m, 3H), 3.09-3.02(m, 2H), 2.89-2.87 (m, 1H), 2.51-2.50 (m, 1H), 2.03-1.75 (m, 6H); LRMS (ESI) m/z 753 (753 calcd for $C_{32}H_{30}Cl_2F_3N_6O_6S$, M+H).

EXAMPLE 21

N-{N-[(3-Cyanobenzene)sulfonyl]-4(R)-[(3S)-3-fluoropyrrolidine]-(L)-prolyl}-4-[(3',5'-dichloroisonicotinoyl)amino]-(L)-phenylalanine ethyl ester

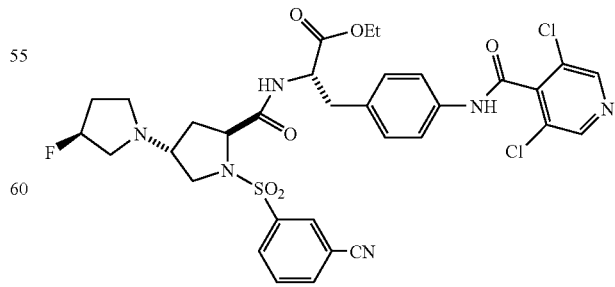

Utilizing the general procedure outlined in Example 1, Steps 2-3, 3,3-difluoropiperidine hydrochloride was exchanged for (3,S)-3-fluoropyrrolidine hydrochloride to give after preparative reverse phase HPLC purification (Phenomenex Synergi 4u Max-RP 80A, 100×20.2 mm, 10:90→80:20 acetonitrile-water 0.01% TFA), the title compound as a white solid: $^1$H NMR (500 MHz, CD$_3$OD) δ 8.62 (s, 2H), 8.16 (s, 1H), 8.09-8.07 (m, 1H), 7.96-7.95 (m, 1H), 7.77-7.71 (m, 2H), 7.56-7.54 (m, 2H), 7.34-7.30 (m, 1H), 5.30-5.25 (m, 1H), 4.89-4.87 (m, 1H), 4.31 (q, 2H), 4.23 (d, 1H), 3.85 (t, 1H), 3.55-3.46 (m, 2H), 3.40-3.37 (dd, 2H), 3.20-3.15 (m,2H), 3.04-3.00 (m, 1H), 2.54-2.50 (m, 1H), 2.35-2.30 (m, 2H), 2.05-1.98 (m, 1H), 1.90-1.85 (m, 1H), 1.39-1.34 (t, 3H); LRMS (ESI) m/z 732 (732 calcd for C$_{33}$H$_{34}$Cl$_2$FN$_6$O$_6$S, M+H).

EXAMPLE 22

N-{N-[(3-Cyanobenzene)sulfonyl]-4(R)-[(3S)-3-fluoropyrrolidine]-(L)-prolyl}-4-[(3',5'-dichloroisonicotinoyl)amino]-(L)-phenylalanine Utilizing the general procedure outlined in Example 2, the title compound was obtained from compound of Example 21 after preparative reverse phase HPLC purification (Phenomenex Synergi 4u Max-RP 80A, 100×20.2 mm, 0:100→80:20 acetonitrile-water 0.01% TFA) as a white solid: $^1$H NMR (500 MHz, CD$_3$OD) δ 8.63 (s, 2H), 8.49-8.48 (m, 1H), 8.11 (s, 1H), 8.00-7.99 (m, 1H), 7.82-7.80 (m, 1H), 7.68-7.63 (m, 3H), 7.38-7.36 (m, 2H), 5.47-5.36 (m, 1H), 4.63-4.58 (m, 2H), 4.09-4.07 (m, 1H), 3.94-3.91 (m, 1H), 3.80-3.40 (m, 5H), 3.31-3.26 (m, 1H), 3.04-3.00 (m, 1H), 2.44-2.25 (m, 4H), LRMS (ESI) m/z 704 (704 calcd for C$_{31}$H$_{30}$Cl$_2$FN$_6$O$_6$S, M+H).

EXAMPLE 23

N-{N-[(3-Cyanobenzene)sulfonyl]-4(R)-[(3R)-3-fluoropyrrolidine]-(L)-prolyl}-4-[(3',5'-dichloroisonicotinoyl)amino]-(L)-phenylalanine ethyl ester

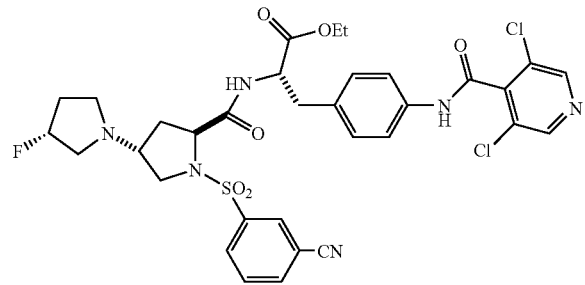

Utilizing the general procedure outlined in Example 1 Steps 2-3, 3,3-difluoropiperidine hydrochloride was exchanged for (3R)-3-fluoropyrrolidine hydrochloride to give after preparative reverse phase HPLC purification (Phenomenex Synergi 4u Max-RP 80A, 100×20.2 mm, 10:90→80:20 acetonitrile-water 0.01% TFA), to afford the title compound as a white solid: $^1$H NMR (500 MHz, CD$_3$OD) δ 8.65 (s, 2H), 8.60-8.59 (m, 1H), 8.16 (m, 1H), 8.04-8.03 (m, 1H), 7.90-7.89 (m, 1H), 7.73-7.66 (m, 3H), 7.38-7.36 (m, 2H), 5.49-5.38 (m, 1H), 4.64-4.62 (m, 2H), 4.19 (q, 2H), 4.10-4.00 (m, 1H), 3.93-3.89 (m, 1H), 3.80-3.70 (m, 1H), 3.65-3.35 (m, 3H), 3.27-3.04 (m, 3H), 2.40-2.29 (m, 4H), 1.33-1.26 (m, 3H), LRMS (ESI) m/z 732 (732 calcd for C$_{33}$H$_{34}$Cl$_2$FN$_6$O$_6$S, M+H).

EXAMPLE 24

N-{N-[(3-Cyanobenzene)sulfonyl]-4(R)-[(3R)-3-fluoropyrrolidine]-(L)-prolyl}-4-[3',5'-dichloroisonicotinoyl)amino]-(L)-phenylalanine Utilizing the general procedure outlined in Example 2, the title compound was obtained from compound of Example 23 after preparative reverse phase HPLC purification (Phenomenex Synergi 4u Max-RP 80A, 100×20.2 mm, 0:100→80:20 acetonitrile-water 0.01% TFA) as a white solid: $^1$H NMR (500 MHz, CD$_3$OD) δ 8.64 (s, 2H), 8.51-8.48 (m, 1H), 8.14 (s, 1H), 8.02-8.00 (m, 1H), 7.85-7.83 (m, 1H), 7.71-7.67 (m, 3H), 7.40-7.39 (m, 2H), 5.50-5.40 (m, 1H), 4.67-4.60 (m, 2H), 4.12-3.80 (m, 1H), 3.92-3.79 (m, 2H), 3.70-3.45 (m, 4H), 3.34-3.29 (m, 3H), 3.06-3.02 (m, 1H), 2.49-2.30 (m, 4H), LRMS (ESI) m/z 704 (704 calcd for C$_{31}$H$_{30}$Cl$_2$FN$_6$O$_6$S, M+H).

EXAMPLE 25

N-{N-[(3-Cyanobenzene)sulfonyl]-4(R)-[4-fluoropiperidine]-(L)-prolyl}-4-[(3',5'-dichloroisonicotinoyl)amino]-(L)-phenylalanine ethyl ester

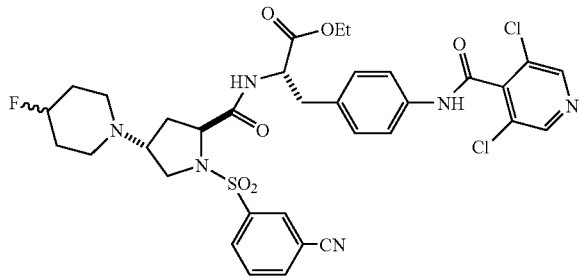

Utilizing the general procedure outlined in Example 1 Steps 2-3, 3,3-difluoropiperidine hydrochloride was exchanged for 4-fluoropiperidine hydrochloride to give the title compound (as a mixture of diastereomers), after preparative reverse phase HPLC purification (Phenomenex Synergi 4u Max-RP 80A, 100×20.2 mm, 10:90→100:0 acetonitrile-water 0.01% TFA), as a white solid: $^1$H NMR (500 MHz, CD$_3$OD) δ 8.63 (s, 2H), 8.58-8.57 (m, 1H), 8.15 (s, 1H), 8.02-8.00 (m, 1H), 7.89-7.87 (m, 1H), 7.71-7.64 (m, 3H), 7.35-7.33 (m, 2H), 4.98-4.81 (m, 1H), 4.61-4.58 (m, 2H), 4.17 (q, 2H), 4.06-3.94 (m, 2H), 3.55-3.51 (m, 1H), 3.34-3.30 (m, 2H), 3.24-3.02 (m, 3H), 2.42-2.30 (m, 2H), 2.20-2.00 (m,3H), 1.38-1.35 (m, 2H), 1.24 (t, 3H); LRMS (ESI) m/z 746 (732 calcd for C$_{34}$H$_{36}$Cl$_2$FN$_6$O$_6$S, M+H).

EXAMPLE 26

N-{N-[(3-Cyanobenzene sulfonyl-4(R)-[4-fluoropiperidine]-(L)-prolyl}-4-(3',5'-dichloroisonicotinoyl)amino]-(L)-phenylalanine Utilizing the general procedure outlined in Example 2, the title compound (as a mixture of diastereomers) was obtained from compound of Example 25, after preparative reverse phase HPLC purification (Phenomenex Synergi 4u Max-RP 80A, 100×20.2 mm, 0:100→80:20 acetonitrile-water 0.01% TFA), as a white solid: $^1$H NMR (500 MHz, CD$_3$OD) δ 8.62 (s, 2H), 8.48-8.47 (m, 1H), 8.12 (s, 1H), 8.00-7.99 (m, 1H), 7.83-7.81 (m, 1H), 7.68-7.64 (m, 3H), 7.38-7.36 (m, 2H), 4.94-4.82 (m, 1H), 4.64-4.57 (m, 2H), 4.04-3.92 (m, 2H), 3.53-3.50 (m, 1H), 3.40-3.26 (m, 5H), 3.04-3.00 (m, 1H), 2.47-2.43 (m, 1H), 2.47-2.05 (m, 5H), LRMS (ESI) m/z 718 (718 calcd for C$_{32}$H$_{32}$Cl$_2$FN$_6$O$_6$S, M+H).

EXAMPLE 27

N-{N-[(3-Cyanobenzene)sulfonyl]-3-[3,3-difluoropyrrolidine]-prolyl}-4-[(3',5'-dichloroisonicotinoyl)amino]-(L)-phenylalanine ethyl ester

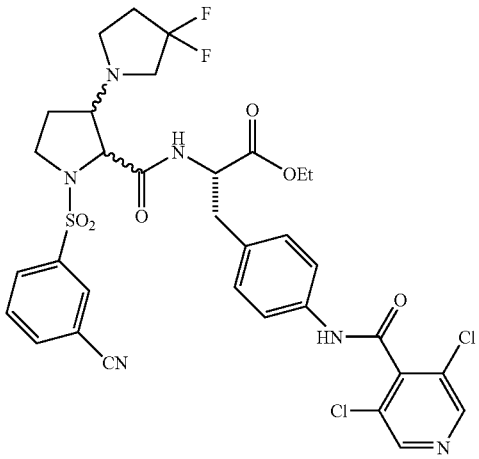

Step 1: Synthesis of N-[(3-Cyanobenzene)sulfonyl]-3-[3,3-difluoropyrrolidine]methyl ester

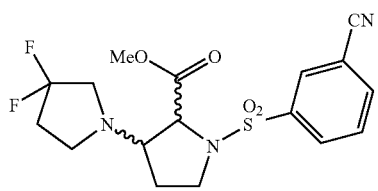

To a solution of (3S)-hydroxy-(L)-proline (Acros, 20 g, 0.15 mol) and sodium carbonate (26 g, 0.25 mol) in 500 mL of water at 0° C. was added powdered 3-cyanobenzenesulfonyl chloride (25 g, 0.12 mol). After stirring at rt overnight, the reaction mixture was acidified with concentrated HCl (pH=3), and the product was extracted with EtOAc (3×100 mL). The organic extracts were dried (MgSO₄), filtered and concentrated to dryness. The residue was then dissolved in methylene chloride (100 mL) and MeOH (100 mL), and was added trimethylsilyldiazomethane (2 Min ether) at 0° C. until a yellow color persisted. After stirring at rt for 15 min, the mixture was concentrated to dryness to give N-[(3-cyanobenzene)sulfonyl]-3(S)-hydroxy-(L)-proline, methyl ester (31.5 g).

To the above compound (31.5 g, 0.10 mol) in 200 mL of EtOAc at 0° C. was added TEA (20 mL, 0.14 mol) and MsCl (9.5 mL, 0.12 mol). After stirring at 0° C. for 20 min, the reaction was quenched with 100 mL of aqueous sodium bicarbonate. After stirring for 15 min, the reaction mixture was partitioned between EtOAc (300 mL) and aqueous sodium bicarbonate (200 mL). The organic layer was separated, washed with brine and concentrated to dryness to give N-[(3-cyanobenzene)sulfonyl]-3(S)-methanesulfonyloxy-(L)-proline, methyl ester (40 g).

To a solution of the above compound (39.5 g, 0.10 mol) in 300 mL of AcCN was added TEA (35 mL, 0.25 mol). After heating at 75° C. for 4 h, the reaction mixture was cooled to rt and concentrated. The residue was dissolved in EtOAc (600 mL) and washed with 1 N aqueous NaOH and brine, and concentrated to dryness to give N-[(3-cyanobenzene)sulfonyl]-2,3-dehydroproline, methyl ester (28 g).

To a suspension of N-[(3-cyanobenzene)sulfonyl]-2,3-dehydroproline methyl ester (0.7 g, 2.4 mmol) in 5 mL of DMF was added 3,3-difluoropyrrolidine hydrochloride salt (2 g, 14.0 mmol) and N,N-diisopropylethylamine (DIPEA) (2.4 mL, 14.0 mmol). After heating at 50° C. for 24 h, the reaction mixture was cooled to room temperature and was concentrated. The residue was purified on silica gel (1:99→30:70 ethyl acetate-hexanes) to afford N-[(3-cyanobenzene)sulfonyl]-3-[3,3-difluoropyrrolidine]methyl ester as a racemic colorless oil mixture: $^1$H NMR (500 MHz, CD₃OD) δ 8.16-8.15 (m, 1H), 8.10-8.08 (m, 1H), 7.88-7.86 (m, 1H), 7.69-7.65 (m, 1H), 4.30 (d, 1H), 3.75 (s, 3H), 3.56-3.47 (m, 2H), 3.14-3.12 (m, 1H), 2.88-2.83 (m, 2H), 2.73-2.70 (m, 2H), 2.19-2.09 (m, 3H), 1.98 (M, 1H); LRMS (ESI) m/z 400 (400 calcd for $C_{17}H_{19}F_2N_3O_4S$, M+H).

Utilizing the general procedure outlined in Example 1, Step 3, methyl (2S,4R)-1-[(3-cyanophenyl)sulfonyl]-4-(3,3-difluoropiperidin-1-yl)pyrrolidine-2-carboxylate was exchanged for N-[(3-cyanobenzene)sulfonyl]-3-[3,3-difluoropyrrolidine]methyl ester to afford the title compound, a white solid, as a mixture of diastereomers: $^1$H NMR (500 MHz, CD₃OD) δ 8.64-8.63 (m, 2H), 8.26-8.24 (m, 1H), 8.16-8.09 (m, 1H), 8.02-8.01 (m, 1H), 7.77-7.73 (m, 1H), 7.61-7.58 (m, 2H), 7.31-7.29 (m, 2H), 4.77-4.74 (m, 1H), 4.24-4.21 (m, 2H), 4.10-4.06 (m, 1H), 3.61-3.49 (m, 1H), 3.33-3.26 (m, 2H), 3.09-3.06 (m, 1H), 2.70-2.51 (m,5H), 1.94-1.88 (m, 4H), 1.30-1.26 (m, 3H); LRMS (ESI) m/z 749 (749 calcd for $C_{33}H_{32}Cl_2F_2N_6O_6S$, M+H).

EXAMPLE 28

N-{N-[(3-Cyanobenzene)sulfonyl]-3-[3,3-difluoropyrrolidine]-prolyl}-4-[(3',5'-dichloroisonicotinoyl)amino]-(L)-phenylalanine Utilizing the general procedure outlined in Example 2, the title compound (as a mixture of diastereomers) was obtained from the compound of Example 27 as a white solid, after preparative reverse phase HPLC purification (Phenomenex Synergi 4u Max-RP 80A, 100×20.2 mm, 20:80→100:0 acetonitrile-water 0.01% TFA): $^1$H NMR (500 MHz, CD₃OD) δ 8.54-8.53 (d, 2H), 8.16-8.10 (m, 1H), 7.90-8.06-7.90 (m, 2H), 7.67-7.61 (m, 1H), 7.51-7.49 (m, 2H), 7.24-7.22 (m, 2H), 4.68-4.61 (m, 1H), 4.09-4.05 (m, 1H), 3.46-3.18 (m, 2.5H), 3.00-2.91 (m, 1.5H), 2.90-2.64 (m, 5H), 1.95-1.82 (m, 4H); LRMS (ESI) m/z 721 (721 calcd for $C_{31}H_{28}Cl_2F_2N_6O_6S$, M+H).

EXAMPLE 29

N-{N-[(3-Cyanobenzene)sulfonyl]-3-[3,3-difluoropiperidinyl]-prolyl}-4-[(3',5'-dichloroisonicotinoyl)-amino]-(L)-phenylalanine ethyl ester

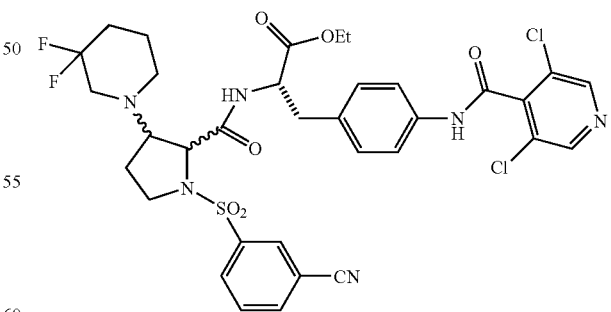

Utilizing the general procedure outlined in Example 27, Steps 1-2,3,3-difluoropyrrolidine hydrochloride was exchanged for 3,3-difluoropiperidine hydrochloride to afford the title compound, a white solid, as a mixture of diastereomers: $^1$H NMR (500 MHz, CD₃OD) δ 8.48-8.47 (d, 2H), 8.07-8.04 (d, 1H), 7.98-7.83 (m, 2H), 7.63-7.56 (m, 1H), 7.46-7.43 (m, 2H), 7.17-7.12 (m, 2H), 4.57-4.50 (m, 1H), 4.10-4.00 (m, 3H), 3.26-3.24 (m, 2H), 3.11-3.09 (m, 1H), 2.86-2.70 (m, 2H), 2.30-2.24 (m, 3H), 2.06-1.90 (m, 1H), 1.73-1.60 (m, 4H), 1.45-1.20 (m, 2H), 1.15-1.07 (m, 3H); LRMS (ESI) m/z 763 (763 calcd for $C_{34}H_{34}Cl_2F_2N_6O_6S$, M+H).

EXAMPLE 30

N-{N-[(3-Cyanobenzene)sulfonyl]-3-[3,3-difluoropiperidinyl]-prolyl}-4-[(3',5'-dichloroisonicotinoyl)amino]-(L)-phenylalanine Utilizing the general procedure outlined in Example 2, the title compound (as a mixture of diastereomers) was obtained from the compound of Example 29 as a white solid: $^1$H NMR (500 MHz, CD$_3$OD) δ 8.52-8.51 (d, 2H), 8.10-8.09 (d, 1H), 8.05-7.93 (dd, 1H), 7.90-7.88 (m, 1H), 7.66-7.61 (m, 1H), 7.48-7.47 (d, 2H), 7.22-7.21 (d, 2H), 4.55-4.50 (m, 1H), 4.03-3.97 (m, 1H), 3.43-3.30 (m, 1H), 3.25-3.15 (m, 2H), 3.00-2.98 (m, 1H), 2.87-2.76 (m, 1H), 2.34-2.26 (m, 3H), 2.06-1.90 (m, 1H), 1.89-1.60 (m, 4H), 1.45-1.20 (m, 2H); LRMS (ESI) m/z 735 (735 calcd for $C_{32}H_{30}Cl_2F_2N_6O_6S$, M+H).

EXAMPLE 31

N-{N-[(3-Cyanobenzene)sulfonyl]-3-[4,4-difluoropiperidinyl]-prolyl}-4-[(3',5'-dichloroisonicotinoyl)amino]-(L)-phenylalanine ethyl ester

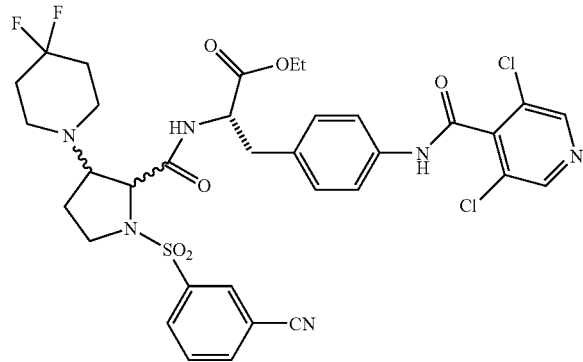

Utilizing the general procedure outlined in Example 27, Steps 1-2,3,3-difluoropyrrolidine hydrochloride was exchanged for 4,4-difluoropiperidine hydrochloride to isolate two isomers: I and II, of the title compound, as a hydrochloride salt after each isomer was treated with 1N hydrochloride in diethyl ether: Isomer I: $^1$H NMR (500 MHz, CD$_3$OD) δ 8.65 (s, 2H), 8.05 (s, 1H), 8.01-8.00 (d, 1H), 7.78-7.76 (d, 1H), 7.69-7.66 (m, 3H), 7.43-7.42 (d, 2H), 4.87-4.84 (m, 1H), 4.63-4.60 (m, 1H), 4.23-4.20 (m, 2H), 4.10-4.09 (m, 1H), 3.85 (m, 1H), 3.71-3.38 (m, 5H), 3.29-3.25 (m, 1H), 3.11-3.08 (m, 1H), 2.52-2.38 (m, 5H), 2.31-2.25 (m, 1H), 1.30-1.26 (t, 3H); LRMS (ESI) m/z 763 (763 calcd for $C_{34}H_{34}Cl_2F_2N_6O_6S$, M+H). Isomer II: $^1$H NMR (500 MHz, CD$_3$OD) δ 8.67 (s, 2H), 8.22 (s, 1H), 8.15-8.13 (d, 1H), 8.04-8.03 (d, 1H), 7.77-7.74 (t, 1H), 7.60-7.59 (d, 2H), 7.32-7.30 (d, 2H), 4.74-4.71 (m, 1H), 4.36-4.31 (m, 2H), 3.85-3.82 (m, 1H), 3.75-3.72 (m, 1H), 3.52-3.29 (m, 7H), 3.07-3.02 (m, 1H), 2.47-2.30 (m, 6H), 1.35-1.33 (t, 3H); LRMS (ESI) m/z 763 (763 calcd for $C_{34}H_{34}Cl_2F_2N_6O_6S$, M+H).

EXAMPLE 32

N-{N-[(3-Cyanobenzene)sulfonyl]-3-[4,4-difluoropiperidinyl]1-prolyl}-4-[(3',5'-dichloroisonicotinoyl)amino]-(L)-phenylalanine Utilizing the general procedure outlined in Example 2, isomer I and isomer II of the compound of Example 31 were converted to the title compound, as a hydrochloride salt after each isomer was treated with 1N hydrochloride in diethyl ether. Acid from isomer I ethyl ester: $^1$H NMR (500 MHz, CD$_3$OD) δ 8.41 (s, 2H), 8.05 (s, 1H), 7.89-7.87 (d, 1H), 7.83-7.81 (d, 1H), 7.59-7.54 (t, 1H), 7.36-7.34 (d, 2H), 7.11-7.09 (d, 2H), 4.35-4.32 (m, 1H), 3.85-3.84 (m, 1H), 3.43-3.10 (m, 3H), 2.92-2.88 (m, 1H), 2.77-2.76 (m, 1H), 2.22-2.19 (m, 2H), 2.08-2.06 (m, 2H), 1.54-1.42 (m, 6H); LRMS-(ESI) m/z 735 (735 calcd for $C_{32}H_{30}Cl_2F_2N_6O_6S$, M+H). Acid from isomer 11 ethyl ester: $^1$H NMR (500 MHz, CD$_3$OD) δ 8.41 (s, 2H), 8.09 (s, 1H), 7.97-7.96 (d, 1H), 7.82-7.81 (d, 1H), 7.58-7.54 (t, 1H), 7.36-7.34 (d, 2H), 7.11-7.10 (d, 2H), 4.39-4.36 (m, 1H), 3.91-3.88 (m, 1H), 3.32-3.28 (m, 1H), 3.21-3.20 (m, 1H), 3.10-3.09 (m, 1H), 2.92-2.91 (m, 1H), 2.72-2.71 (m, 1H), 2.14-2.12 (m, 2H), 2.04-2.01 (m, 2H), 1.80-1.77 (m, 1H), 1.63-1.53 (m, 1H), 1.47-1.41 (m, 4H); LRMS (ESI) m/z 735 (735 calcd for $C_{32}H_{30}Cl_2F_2N_6O_6S$, M+H).

EXAMPLE 33

N-{N-[(3-Cyanobenzene)sulfonyl]-4(R)-[tert-butyl 1'-pyrrolidine-2' (R)-carboxylate]-(L)-prolyl}-4-[(3", 5"-dichloroisonicotinoyl)amino]-(L)-phenylalanine ethyl ester

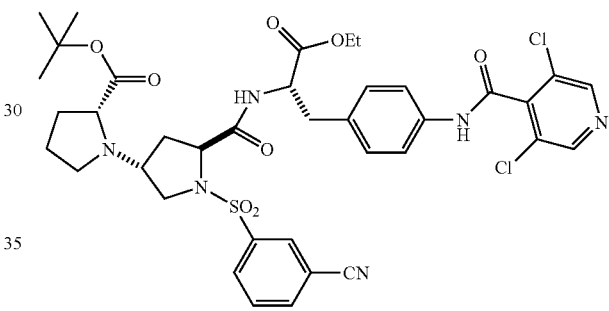

Utilizing the general procedure outlined in Example 1, Steps 2-3, 3,3-difluoropiperidine hydrochloride was exchanged for tert-butyl D-prolinate to give after preparative reverse phase HPLC purification (Phenomenex Synergi 4u Max-RP 80A, 100×20.2 mm, 20:80→90:10 acetonitrile-water 0.01% TFA), the title compound as a white solid: $^1$H NMR (500 MHz, CD$_3$OD) δ 8.63 (s, 2H), 8.55-8.54 (m, 1H), 8.13 (s, 1H), 8.03-8.01 (m, 1H), 7.87-7.85 (m, 1H), 7.71-7.64 (m, 3H), 7.35-7.33 (m, 2H), 4.61-4.59 (m, 2H), 4.22-4.16 (m, 3H), 4.10-4.00 (m, 1H), 3.88-3.84 (m, 1H), 3.59-3.51 (m, 2H), 3.24-3.20 (m, 2H), 3.04-3.01 (m, 1H), 2.50-2.41 (m, 1H), 2.26-2.22 (m,2H), 2.12-2.10 (m, 2H), 2.00-1.94 (m, 1H), 1.50 (s, 9H), 1.25 (t, 3H); LRMS (ESI) m/z 814 (814 calcd for $C_{38}H_{43}Cl_2N_6O_8S$, M+H).

EXAMPLE 34

N-{N-[(3-Cyanobenzene)sulfonyl]-4(R)-[tert-butyl 1'-pyrrolidine-2'(R)-carboxylate]-(L)-prolyl}-4-[(3", 5"-dichloroisonicotinoyl)amino]-(L)-phenylalanine Utilizing the general procedure outlined in Example 2, the title compound was obtained from the compound of Example 33, after preparative reverse phase HPLC purification (Phenomenex Synergi 4u Max-RP 80A, 100×20.2 mm, 0:100→80:20 acetonitrile-water 0.01% TFA), as a white solid: $^1$H NMR (500 MHz, CD$_3$OD) δ 8.62 (s, 2H), 8.47-8.45 (m, 1H), 8.10 (s, 1H), 8.02-8.00 (m, 1H), 7.81-7.79 (m, 1H), 7.69-7.64 (m, 3H), 7.37-7.36 (m, 2H), 4.63-4.57 (m, 2H), 4.32-4.29 (m, 1H), 4.15-4.05 (m, 1H), 3.88-3.84 (m, 1H), 3.68-3.60 (m, 1H), 3.56-3.52 (m, 1H), 3.31-3.26 (m, 2H), 3.02-2.98 (m, 1H), 2.53-2.45 (m,1H), 2.31-2.10 (m, 4H), 2.00-1.94 (m, 1H), 1.50 (s, 9H); LRMS (ESI) m/z 786 (786 calcd for $C_{36}H_{38}Cl_2N_6O_8S$, M+H).

EXAMPLE 35

N-{N-[(3-Cyanobenzene)sulfonyl]-4(R)-[1'-pyrrolidine-2'(R)-carboxylic acid]-(L)-prolyl}-4-[(3",5"-dichloroisonicotinoyl)amino]-(L)-phenylalanine

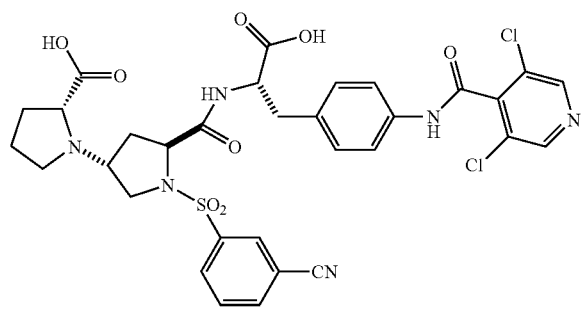

To the solid compound of Example 34 (86 mg, 0.1 mmol), trifluoroacetic acid (2.5 ml) was added. After 4 h, the reaction was concentrated to give after preparative reverse phase HPLC purification (Phenomenex Synergi 4u Max-RP 80A, 100×20.2 mm, 0:100→80:20 acetonitrile-water 0.01% TFA), the title compound as a white solid: $^1$H NMR (500 MHz, $CD_3OD$) δ 8.62 (s, 2H), 8.48-8.47 (m, 1H), 8.10 (s, 1H), 8.01-7.97 (m, 1H), 7.82-7.80 (m, 1H), 7.69-7.61 (m, 3H), 7.38-7.36 (m, 2H), 4.63-4.58 (m, 2H), 4.44-4.41 (m, 1H), 4.22-4.12 (m, 1H), 3.90-3.86 (m, 1H), 3.69-3.62 (m, 1H), 3.61-3.58 (m, 1H), 3.33-3.26 (m, 2H), 3.03-2.98 (m, 1H), 2.59-2.48 (m,1H), 2.37-2.10 (m, 4H), 2.00-1.89 (m, 1H); LRMS (ESI) m/z 730 (730 calcd for $C_{32}H_{31}Cl_2N_6O_8S$, M+H).

What is claimed is:

1. N-{N-[(3-Cyanobenzene)sulfonyl]-4(R)-[3,3-difluoropiperidinyl]-(L)-prolyl}-4-[(3',5'-dichloroisonicotinoyl) amino]-(L)-phenylalanine ethyl ester and pharmaceutically acceptable salts thereof 2. N-{N-[(3-Cyanobenzene)sulfonyl]-4(R)-[3,3-difluoropiperidinyl ]-(L)-prolyl}-4-[(3',5'-dichloroisonicotinoyl) amino]-(L)-phenylalanine and pharmaceutically acceptable salts thereof.

* * * * *